United States Patent
Puleo et al.

(10) Patent No.: US 12,370,383 B2
(45) Date of Patent: Jul. 29, 2025

(54) NEUROMODULATION TO TREAT PHYSIOLOGICAL CONDITIONS

(71) Applicants: General Electric Company, Schenectady, NY (US); ALBANY MEDICAL COLLEGE, Albany, NY (US)

(72) Inventors: Christopher Michael Puleo, Niskayuna, NY (US); Victoria Eugenia Cotero, Niskayuna, NY (US); Tzu-Jen Kao, Niskayuna, NY (US); Jeffrey Michael Ashe, Niskayuna, NY (US); Damian Seyung-Ho Shin, Albany, NY (US)

(73) Assignees: General Electric Company, Schenectady, NY (US); Albany Medical College, Albany, NY (US)

( * ) Notice: Subject to any disclaimer, the term of this patent is extended or adjusted under 35 U.S.C. 154(b) by 149 days.

(21) Appl. No.: 17/917,539

(22) PCT Filed: Apr. 6, 2021

(86) PCT No.: PCT/US2021/025922
§ 371 (c)(1),
(2) Date: Oct. 6, 2022

(87) PCT Pub. No.: WO2021/207161
PCT Pub. Date: Oct. 14, 2021

(65) Prior Publication Data
US 2023/0140990 A1 May 11, 2023

Related U.S. Application Data

(60) Provisional application No. 63/027,724, filed on May 20, 2020, provisional application No. 63/007,766, filed on Apr. 9, 2020.

(51) Int. Cl.
A61N 7/00 (2006.01)
A61B 8/00 (2006.01)
A61B 8/08 (2006.01)

(52) U.S. Cl.
CPC .............. *A61N 7/00* (2013.01); *A61B 8/08* (2013.01); *A61B 8/469* (2013.01); *A61B 8/54* (2013.01); *A61N 2007/0026* (2013.01)

(58) Field of Classification Search
CPC .............................. A61B 8/54; A61B 8/469
See application file for complete search history.

(56) References Cited

U.S. PATENT DOCUMENTS 9,199,097 B2  12/2015  Gertner
2010/0234728 A1  9/2010  Foley et al.
(Continued)

FOREIGN PATENT DOCUMENTS

WO  2019-173518 A1  9/2019

OTHER PUBLICATIONS

Search report for PCT/US2021/025922 mailed on Jul. 27, 2021.
EP application 21784053.7 filed Nov. 2, 2022—extended Search Report issued Mar. 15, 2024; 6 pages.

*Primary Examiner* — Keith M Raymond
*Assistant Examiner* — Nyrobi Celestine
(74) *Attorney, Agent, or Firm* — Fletcher Yoder, P.C.

(57) ABSTRACT

The subject matter of the present disclosure generally relates to techniques for applying focused ultrasound energy to a region of interest in a subject to induce neuromodulation of the celiac plexus to treat inflammatory bowel disease. The region of interest ay include at least a portion of a peripheral ganglion of the celiac plexus.

16 Claims, 20 Drawing Sheets

(56) References Cited

U.S. PATENT DOCUMENTS

| | | | | |
|---|---|---|---|---|
| 2013/0178910 | A1* | 7/2013 | Azamian | A61K 9/0019 |
| | | | | 607/33 |
| 2014/0236048 | A1* | 8/2014 | Gertner | A61B 5/4839 |
| | | | | 601/2 |
| 2015/0080926 | A1* | 3/2015 | Emery | A61N 7/02 |
| | | | | 606/169 |
| 2017/0007853 | A1* | 1/2017 | Alford | A61B 8/02 |
| 2018/0028841 | A1* | 2/2018 | Konofagou | A61B 8/085 |
| 2018/0117319 | A1* | 5/2018 | Chew | A61N 1/3605 |
| 2018/0236235 | A1* | 8/2018 | Hettrick | A61N 1/36082 |
| 2019/0069949 | A1* | 3/2019 | Vrba | A61B 18/02 |
| 2019/0269942 | A1 | 9/2019 | Alford et al. | |
| 2019/0321640 | A1* | 10/2019 | Carmena | A61N 1/37223 |
| 2020/0046992 | A1* | 2/2020 | Tracey | A61B 5/6825 |
| 2020/0054228 | A1 | 2/2020 | Puleo et al. | |
| 2020/0085809 | A1* | 3/2020 | Bright | A61P 29/00 |
| 2020/0230408 | A1* | 7/2020 | Errico | A61N 1/36014 |
| 2020/0337765 | A1* | 10/2020 | Smith | A61B 18/1492 |

* cited by examiner

NEUROMODULATION TO TREAT PHYSIOLOGICAL CONDITIONS

CROSS-REFERENCE TO RELATED APPLICATIONS

The present application claims priority to and the benefit of U.S. Provisional Application No. 63/007,766, filed on Apr. 9, 2020, and U.S. Provisional Application No. 63/027,724, filed on May 20, 2020.

BACKGROUND

The subject matter disclosed herein relates to neuromodulation and more specifically, to techniques for modulating a physiological response using energy applied from an energy source.

Neuromodulation has been used to treat a variety of clinical conditions. For example, electrical stimulation at various locations along the spinal cord has been used to treat chronic back pain. An implantable device may periodically generate electrical energy that is applied to a tissue to activate certain nerve fibers, which may result in a decreased sensation of pain. With regard to spinal cord stimulation, the stimulating electrodes are generally positioned in the epidural space, although the pulse generator may be positioned somewhat remotely from the electrodes, e.g., in the abdominal or gluteal region, but connected to the electrodes via conducting wires. In other implementations, deep brain stimulation may be used to stimulate particular areas of the brain to treat movement disorders, and the stimulation locations may be guided by neuroimaging. Such central nervous system stimulation is generally targeted to the local nerve or brain cell function and is mediated by electrodes that deliver electrical pulses and that are positioned at or near the target nerves. However, positioning electrodes at or near the target nerves is challenging. For example, such techniques may involve surgical placement of the electrodes that deliver the energy. In addition, specific tissue targeting via neuromodulation is challenging. Electrodes that are positioned at or near certain target nerves mediate neuromodulation by triggering an action potential in the nerve fibers, which in turn results in neurotransmitter release at a nerve synapse and synaptic communication with the next nerve. Such propagation may result in a relatively larger or more diffuse physiological effect than desired, as current implementation of implanted electrodes stimulate many nerves or axons at once. Because the neural pathways are complex and interconnected, a more selective and targeted modulated effect may be more clinically useful.

BRIEF DESCRIPTION

Certain embodiments are summarized below. These embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a method is provided that includes applying focused ultrasound energy to a region of interest in a subject to induce neuromodulation of one or more nerve pathways, wherein the region of interest comprises at least a portion of a celiac plexus.

In one embodiment, a system is provided that includes an ultrasound probe configured to apply focused ultrasound energy to a region of interest comprising at least a portion of a celiac plexus in a subject to neuromodulate a peripheral ganglion of the celiac plexus of the subject. The system also includes a controller that is configured to acquire image data of the subject from the ultrasound probe operating in an imaging mode, select the region of interest based on the image data; and control the ultrasound probe to apply the focused ultrasound energy to the region of interest as part of a treatment protocol to treat inflammatory bowel disease in the subject.

In one embodiment, a method is provided that includes acquiring image data of a subject from an ultrasound probe operating in an imaging mode, wherein the subject is diagnosed with inflammatory bowel disease; selecting a region of interest comprising at least a portion of the celiac plexus based on the image data; and controlling the ultrasound probe to apply focused ultrasound energy to the region of interest as part of a treatment protocol to treat the inflammatory bowel disease, wherein the region of interest comprises at least a portion of a peripheral ganglion of a celiac plexus

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
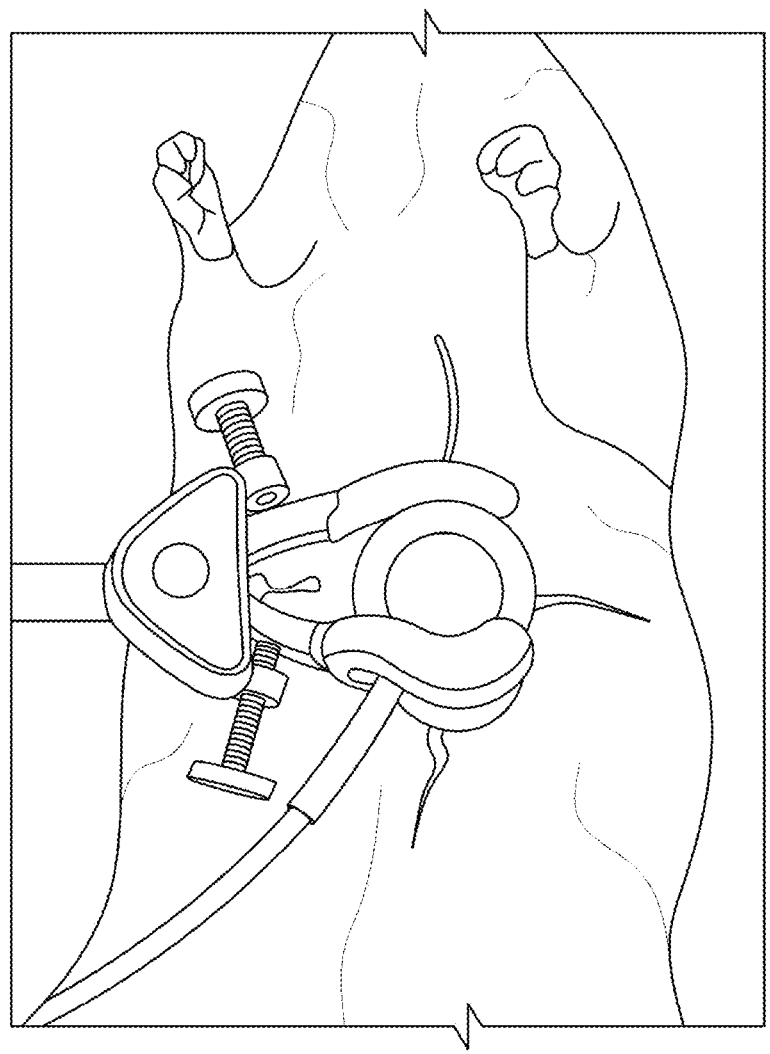
FIG. 1 is a schematic illustration of an experimental setup for ultrasound energy application according to embodiments of the disclosure.

One or more specific embodiments are described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to, "for example", "for instance", "such as", "e.g.", "including", "in certain embodiments", "in some embodiments", and "in one (an) embodiment."

When introducing elements of various embodiments of the present disclosure, the articles "a", "an", "the", and "said" are intended to mean that there are one or more of the elements. The terms "comprising", "including", and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Inflammatory bowel disease (IBD) subsumes a series of chronic and relapsing gastrointestinal (GI) disorders with Crohn's disease (CD) and ulcerative colitis (UC) being the two major notable mentions. IBD causes chronic inflammation to the GI tract with symptoms comprising of persistent diarrhea, abdominal pain, hemorrhaging and/or rectal bleeding. Many IBD symptoms also manifest outside of the GI tract including arthritis, episcleritis and fatigue. As of 2015, there were approximately 3 million adults in the United States diagnosed with IBD, which represents approximately 1% of the country's population. The increasing number of diagnoses in recent years has positioned IBD as a global health problem with estimates of a 20% increase in new diagnoses occurring per decade, which also creates a considerable economic burden.

Despite efforts, treatment options for IBD are notably lacking in availability and/or efficacy. Many patients become refractory to first-line pharmacotherapeutics or develop further complications such as strictures, perforations or fistulas, which may then necessitate a recommendation for surgery. The recent introduction of anti-tumor necrosis factor (TNF) agents for IBD has been a major advance in treating this disease, but rates of non-responders can be as high as 60%. Additionally, 30% of individuals become refractory to treatments within 12 months of administration and relapse with re-emergent symptomatology. Given that hospitalization and surgery rates for IBD have not decreased and data posit moderate increases in rates of hospitalization and surgery for CD and UC only further underscores the unmet need and clinical utility to develop new therapeutic interventions to treat IBD.

There are a variety of etiological components which contribute to the development of IBD involving complex interactions between genetic, immunological and environmental conditions. In the absence of a single underlying pathophysiological mechanism for IBD, the consensus among the field is that particular environmental triggers upset the intestinal homeostasis in individuals with inherent susceptibility to chronic disruption of the immune system and/or disturbed interactions with gut flora resulting in inflammatory-mediated injury.

A direct connection between the central nervous system (CNS) and immune system may involve the spleen for feedback-controlled regulation of cytokine release from splenic and circulating macrophages. This is particularly relevant to IBD due to the role of dysregulated cytokine levels in modulating intestinal inflammation and colonic injury. Sensory nerve feedback from circulating cytokines/endotoxins may trigger vagal-mediated signaling to splenic macrophages to dampen inflammatory responses. This could occur indirectly through adrenergic neurons in the celiac plexus within the cholinergic anti-inflammatory pathway (CAP). In light of this, the peripheral pathway may serve as a target for novel bioelectric therapeutics, but current electrical stimulators are unable to administer enteric stimulation.

Provided herein are techniques to use focused ultrasound to neuromodulate the celiac plexus (or at least a portion of the celiac plexus) with the goal of improving IBD-like symptomology. Disclosed herein are results of studies in a rat model of colitis, which involves animals drinking dextran sulfate sodium (DSS) daily via their drinking bottle. The studies assessed endpoint metrics routinely used in rodent models of IBD with or without focused ultrasound administration. Focused ultrasound as provided herein was shown to improve IBD-like symptomology such as stool consistency, gross bleeding/diarrhea and colon tissue integrity in the DSS rat model of colitis. Efficacy was noted in both the 'mild' and 'severe' versions of IBD revealed by using different formulations of DSS. These results demonstrate clinical utility for non-invasive focused ultrasound neuromodulation in IBD. Focused ultrasound may be used to target specific plexus or ganglion in the peripheral nervous system for diseases such as IBD.

FIG. 1 shows an experimental setup used to perform certain neuromodulation experiments focused on a target (e.g., a celiac plexus) as provided herein. An energy application device operated according to parameters set by a controller to apply focused ultrasound to a region of interest to target to the celiac plexus. In rats, this area is located just below the diaphragm. The ultrasound transducer placement on the rat was determined by initial ultrasound imaging, shown in FIG. 2, which revealed two major arteries, hepatic and splenic, as landmarks used in locating the celiac plexus. After, the transducer was positioned just lateral to the xiphoid process approximately 25 mm above the celiac plexus to activate the enteric CAP pathway at the level of the superior mesenteric ganglion.

All experiments involving animals complied with the National Institutes of Health and Albany Medical College (AMC) Institutional Animal Care and Use Committee (IACUC) guidelines. Animals were purchased from Taconic Biosciences (Germantown, NY, USA) with procedures performed during the light phase (7:00 AM to 7:00 PM) of the light-dark cycle. Animals had access to food and liquid ad libitum.

Figure 2:
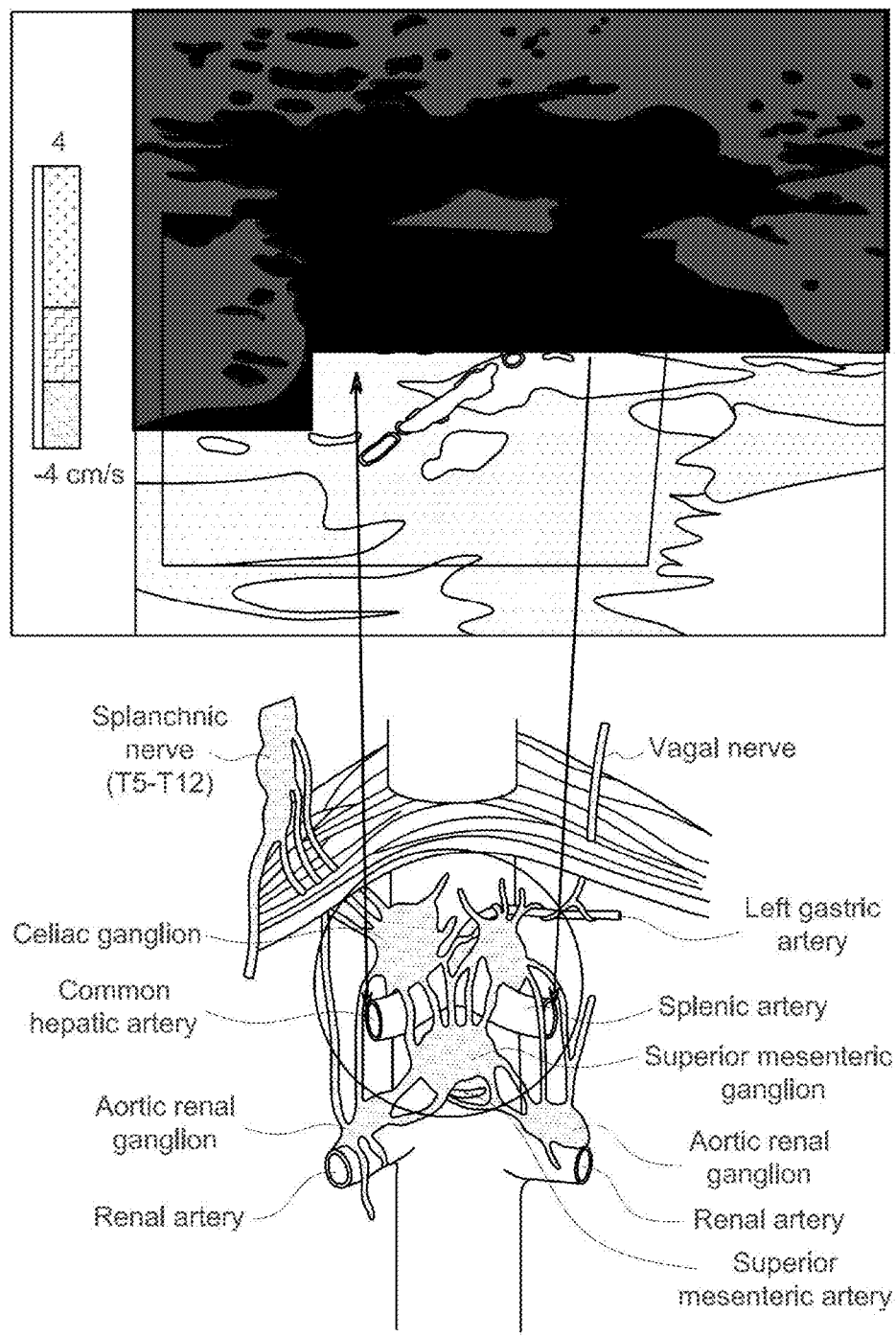
FIG. 2 shows ultrasound imaging used to spatially select a region of interest for ultrasound energy application.

Male Sprague Dawley rats with an initial weight of 200-350 g were anesthetized by placing them in an inhalant chamber filled with 4% isoflurane set to 2-3 L/min (Harvard Apparatus, MA, USA) so they could be easily handled for a photo of the animals' anus, followed by a collection of stool specimen to be tested for consistency and blood analysis. Immediately after, the head of the rat was placed in a sealed nose cone while positioned on its back and anesthesia was maintained with 1.5% isoflurane at 2-3 L/min via a tabletop vaporizer (Harvard Apparatus, MA, USA). The abdomen, specifically the area above the xiphoid process, was shaved and marked with a black pen to target the transducer for focused ultrasound administration. This location targets the anterior vagal trunk, which is proximal to the superior mesenteric and both the left and right celiac ganglion as noted using an ultrasound imaging applicator (FIG. 2). After focused ultrasound was applied, rats were taken off the isoflurane anesthesia, weighed and returned to their individual cages.

A Dextran Sulfate Sodium (DSS) model was used to induce IBD-like pathophysiology in the rats. Dextran Sulfate Sodium (DSS) is a water-soluble, sulfated polysaccharide that induces intestinal inflammation in rats when ingested daily in solution with water over time. This stems from DSS being an epithelial cell irritant which concentrates in the large bowel resulting in ulcerated lesions throughout the colonic lamina propria. This induces IBD-like pathophysiology and symptomology by damaging the epithelial barrier and enabling entry of luminal bacteria/antigens into the mucosa. Moreover, mucosal lesions also increase in number and size in the distal colon, eliciting epithelial damage which resembles that seen in human ulcerative colitis. DSS is a model for acute, chronic and/or relapsing intestinal inflammation.

On day 1 of the experiment, animals had DSS added to their drinking water containing normal tap water, which was available ad libitum. Concentrations ranged from 4-9% depending on the experiment. Animals in the control groups only drank tap water. For all groups, the drinking bottle was changed every 3-5 days to ensure that the DSS in the water bottles was not degraded and free from bacterial contamination which would affect DSS-induced symptoms.

An endpoint metric to assess symptomology in rodent models of IBD is the disease activity index (DAI), which may be used as a metric to assess effectiveness and/or success of neuromodulation as provided herein. DAI scores were assessed using weight loss, stool consistency and gross bleeding. Each criterion can range from 0-4 to reflect normal to the most severe symptomology, respectively. Weight loss was scored relative to baseline weights. This semi-quantitative analytic tool is composed of daily measurements of animal weight, stool consistency and the presence of blood in feces and rectal bleeding with criteria as follows (Table 1):

TABLE 1

DAI scores

| SCORE | WEIGHT LOSS (%) | SCORE | STOOL CONSISTENCY | SCORE | GROSS BLEEDING IN STOOL |
|---|---|---|---|---|---|
| 0 | None | 0 | Normal | 0 | None |
| 1 | 1-5 | 1 | | 1 | |
| 2 | 5-10 | 2 | Loose | 2 | Slight |
| 3 | 10-15 | 3 | | 3 | |
| 4 | >15 | 4 | Watery | 4 | Heavy |

Weight loss rated from 0 points to 4 points representing no weight loss (score 0) to more than 15% weight loss (score 4); stool consistency rated from 0 points to 4 points representing normal texture and appearance (score 0) to watery diarrhea (score 4); rectal bleeding rated from 0 points to 4 points spanning no bleeding (score 0), slight bleeding (score 2) to gross bleeding (score 4). Taken together, a maximum total DAI score of 12 points is possible from the 3 sub-categories.

Animal body weight was monitored each day to assess for presence and magnitude of weight loss. Stool consistency and gross bleeding were visually assessed with photos taken as digital records. Stool samples were additionally tested for blood using a fecal blood detection test (Sure-Vue Fecal Occult Blood Slide Test System; Fisher Scientific, Hampton, NH). If bleeding was not visible but the occult blood test was positive, the bleeding score was incremented by 1 point. In addition to DAI metrics, liquid consumption for 12 days was also recorded.

After two weeks of drinking DSS and having been treated with focused ultrasound or not, rats were sacrificed. The colon was collected for post-mortem analyses such as colon length comparisons, cytokines, and histological damage including epithelial damage and inflammatory cell infiltration.

Due to spatial limitations with focused ultrasound in size/scale of the rat anatomy, the enteric CAP pathway was targeted by modulating the celiac plexus (left and right celiac ganglia and/or superior mesenteric ganglion) with the focused ultrasound transducer probe positioned in the left ventral area between the xiphoid process and the lower rib cage under isoflurane-mediated anesthesia (FIG. 1).

The focused ultrasound system consisted of a function generator (Agilent 33120A), a radio frequency (RF) power amplifier (ENI 350L) and a custom-made 2.5 MHz, focused ultrasound (FUS) transducer. The FUS transducer was 0.75 inches tall and 0.75 inches in diameter with a curved surface and a transducer focus depth of focus 25.4 mm. The FUS transducer was acoustically coupled to the animal through an ultrasound gel placed on the shaved abdomen. The function generator produced a pulsed sinusoidal waveform potentiated by the RF power amplifier and transmitted to the FUS transducer. FUS stimulation allowed the targeting of specific locations, unlike previous ultrasound techniques that required a transducer to be swept across an organ or left in place as unfocused ultrasound with a 5 $cm^2$ footprint.

Every day, 3 minutes of focused ultrasound was applied to the target area (Carrier Frequency: 2.5 MHZ, Amplitude: 300 mV, Burst Length: 300 carrier cycles, Burst Repetition Period: 200 milliseconds). At the Carrier Frequency of 2.5 MHZ, each carrier cycle is 0.4 microseconds and 300 carrier cycles is 120 microseconds in duration. Therefore, during each 200 millisecond Burst Repetition Period, the transducer is actively pulsing for 120 microseconds and remains inactive for the remaining 199.88 milliseconds before repeating the next burst. Animals were separated into different groups delineated by their treatment and control variables (Table 2). Animal groups were assigned according to their disease condition and treatment. The left column has the animal group names, the middle column describes the treatments.

TABLE 2

Animal Groups

| ANIMAL GROUPS | DESCRIPTION OF TREATMENTS |
|---|---|
| DSS | Rats drinking DSS each day for two weeks |
| DSS + 1X FUS | Rats drinking DSS with non-invasive FUS once each day for two weeks; under isoflurane during non-invasive FUS administration |
| DSS + 2X FUS | Rats drinking DSS with non-invasive FUS twice each day separated by six hours per day for two weeks; under isoflurane during non-invasive FUS administration |
| DSS + mock 1X FUS | Rats drinking DSS under isoflurane anesthesia once each day for two weeks |
| DSS + mock 2X FUS | Rats drinking DSS under isoflurane anesthesia twice each day separated by six hours per day for two weeks |
| Naïve | Rats drinking water only for two weeks |
| Water + 1X FUS | Rats drinking water with non-invasive FUS once each day for two weeks; under isoflurane during non-invasive FUS administration |
| Water + 2X FUS | Rats drinking water with non-invasive FUS twice each day separated by six hours per day for two weeks; under isoflurane during non-invasive FUS administration |
| Water + mock 1X FUS | Rats drinking water under isoflurane anesthesia once each day for two weeks |
| Water + mock 2X FUS | Rats drinking water under isoflurane anesthesia twice each day separated by six hours per day for two weeks |

A total of 60 rats were divided into the following groups: Animals drinking Dextran Sulfate Sodium labeled as 'DSS'. Animals given non-invasive focused ultrasound are in the 'FUS' group. As a sham control group for focused ultrasound labeled as 'mock FUS', rats underwent the same procedures as those receiving focused ultrasound such as a shaved abdomen and anesthetized with isoflurane, marked with a pen with the transducer probe positioned in the same spot between the xiphoid process and lower ribs. However, the RF power amplifier, function generator and transducer were turned off. Animals not given DSS or focused ultrasound and only removed from their cage once daily to monitor weight change and assess stool consistency and gross bleeding scores were labeled as 'Naïve'. Animals who underwent twice-daily non-invasive focused ultrasound were denoted with '2x' before their treatment designation. Specific to animals in the '2×FUS' group, rats received two focused ultrasound treatments each day with the first applied in the morning and the second focused ultrasound session performed in the afternoon approximately 6 hours after the first focused ultrasound session. The settings for the second focused ultrasound were identical to the first focused ultrasound given in the morning, but no endpoint metrics were not collected during the second focused ultrasound treatment. Labels were also combined for some animal groups to reflect receiving multiple procedures. For instance, rats drinking DSS but receiving two sham focused ultrasound procedures every day were denoted as 'DSS+2× mock FUS'.

Figure 17:
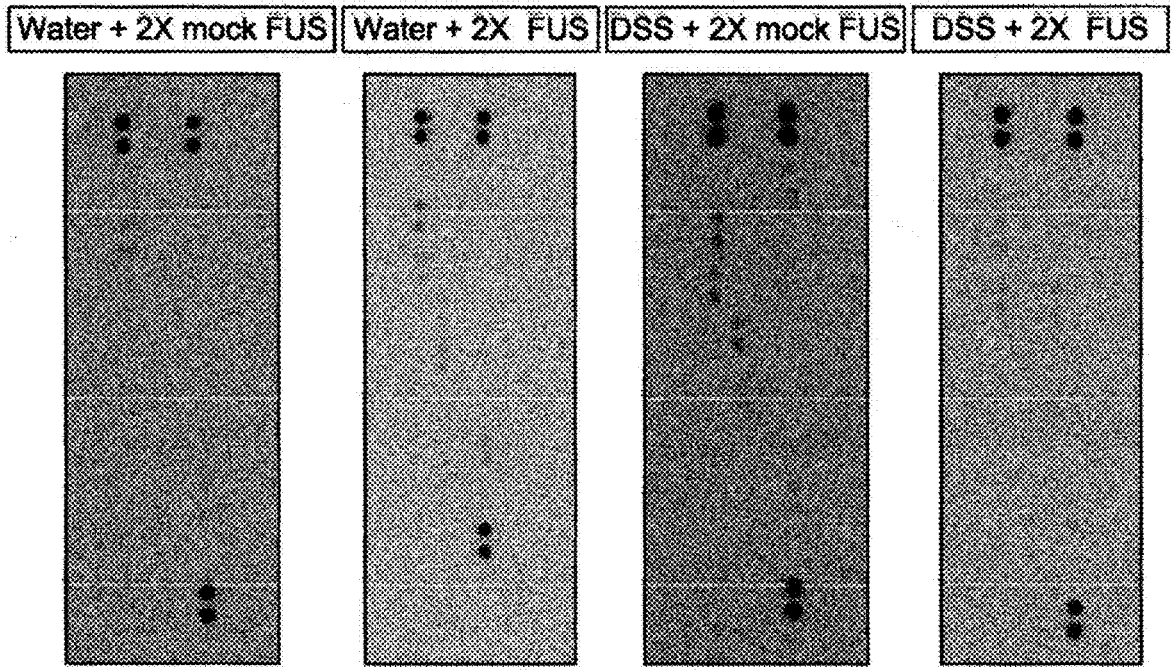
FIG. 17 shows array coordinates and array data for rat cytokine activity assessed from the colon of rats in the "Naïve", "Water+2×FUS", "DSS+2× mock FUS" and "DSS+2×FUS" groups.

After experiments were completed, animals were anesthetized with an IP injection of urethane in saline (1.2-1.5 g/kg) followed by a thoracotomy and a dissection to remove the colon from the cecum to the anus. Photos were taken before and after the colon was flushed with 1× phosphate buffer solution (PBS). The colon was segmented into 3 sections approximately 20 mm long with the proximal portion close to the cecum, the distal portion near the anus and the central portion in-between the two ends. Each section was weighed, snap frozen in liquid nitrogen and stored at −80° C. until tissue was homogenized using a lysis buffer (Tissue Extraction Reagent I, Invitrogen, Vienna, Austria) with an inhibitor cocktail and Ethylenediaminetetraacetic acid (Halt™ Protease Inhibitor Cocktail, Thermo Scientific, Rockford, IL USA) for cytokine analyses. After, samples were centrifuged at 10,000 g for 30 minutes at 4° C., the supernatant was collected and stored at −80° C. Protein concentration was analyzed using a Bicinchoninic acid assay (BCA) and cytokine activity assessed with a proteome profiler rat cytokine array kit (R&D systems, Minneapolis, MN). This rat cytokine array kit comprised of control antibodies in duplicate on a nitrocellulose membrane. A blocking buffer was added to a 4-well plate and membranes were incubated for an hour. A solution containing 26 different biotinylated detection antibodies (400 μg/μl) was incubated at room temperature for an hour and replaced the blocking buffer removed from the wells. The membranes were placed on a shaker (Microjive shaker, Boekel Scientific, Feasterville, PA) and incubated overnight at −4° C. The next day, membranes were washed 3× with the wash buffer to remove unbound material. After, streptavidin-HRP and chemiluminescent detection reagents were added to the membrane which resulted in the appearance of dots. The position, size and color of these corresponded to the quantity of bound select cytokines (see FIGS. 17-18). Membranes were scanned using a digital block scanner (ChemiDoc Western Blot Digital imaging system, Bio-Rad, Hercules, CA) and analyzed using HLImage++(Western Vision Software, Salt Lake City, UT).

Sections of the rectum and adjacent 1.5 cm of colon tissue was also acquired and preserved in 4% paraformaldehyde (PFA), transferred to 70% ethanol for hematoxylin and eosin (H&E) staining and embedded in paraffin. This tissue was sectioned longitudinally at 5 μm thick and placed on charged microscope slides (Globe Scientific; Mahway, NJ).

Slides were dewaxed in xylene washed three times, followed by a series of alcohol rinses at 100% ethanol (2×) and 95% ethanol (2×) to hydrate the tissue. The slides were placed in hematoxylin 7211 and differentiated following a bluing reagent bath using Eosin-Y. Prior to the Eosin-Y rinse, slides were given a 95% alcohol wash once. The slides were then dehydrated again by placing the slides in a 100% ethanol wash three times and cleared with a xylene substitute wash before being cover-slipped with Cytoseal 60 (Fisher Scientific, Hampton, NH).

The hematoxylin-eosin Y stained sections were used to assess the infiltration of inflammatory cells, crypt distortion and erosion using a semi-quantitative scoring rubric. (Table 3). Histological disease severity was assessed using a scoring rubric from 0 to 4 for epithelial damage and infiltration of inflammatory cells. The sum of both scores are combined to provide a histological overall damage score of 8. The center column describes the magnitude of epithelial damage based on morphology, goblet cell loss, loss of crypts and loss of crypts in large areas. The right column describes the severity of infiltration of inflammatory cells based on the depth of penetration into the various colon layers.

TABLE 3

Scoring for stained sections

| Score | Epithelial Damage (E) | Infiltration (I) |
|---|---|---|
| 0 | Normal Morphology | No infiltrate |
| 1 | Loss of goblet cells | Infiltrate around the crypt basis |
| 2 | Loss of goblet cells in large areas | Infiltrate reaching to muscularis mucosae |
| 3 | Loss of crypts | Extensive infiltration of reaching the muscularis mucosae, thickening of the mucosa with abundant edema |
| 4 | Loss of crypts in large area | Infiltration of the submucosa |

Specifically, epithelial damage and infiltration were scored independently based on 0 to 4 scales with: 0=normal morphology; 1=loss of goblet cells; 2=loss of goblet cells in large areas; 3=loss of crypts; 4=loss of crypts in large areas. Scores for infiltration were designated as follows: 0=no infiltrate; 1=infiltrate around the crypt basis; 2=infiltrate reaching to muscularis mucosae; 3=extensive infiltration reaching the lamina muscularis mucosae and thickening of the mucosa with abundant edema; 4=infiltration of the lamina submucosa. The sum of both epithelium damage and infiltration results in a total histopathological maximum score of 8.

The DSS chemical coinciding with IBD symptomology deemed as 'Mild' was purchased from Sigma-Aldrich (MW: >500 kDA, Lot #BCBZ5763). The DSS chemical which induced 'Severe' IBD symptomology was purchased from Fisher Scientific (MW: 35-50 kDa, item #AAJ6360622). Unless stated otherwise, all other chemicals were purchased from Sigma-Aldrich with chemicals and drugs purchased elsewhere are noted in the text.

DAI, stool consistency and gross bleeding were assessed by at least two unblinded lab personnel while the histopathological tissue was scored by two blinded lab personnel. Data were analyzed using a two-way analysis of variance (ANOVA) with Graphpad Prism software (v8.3.0; San Diego, CA) with repeated measures when possible and a post hoc analysis using a Fisher's LSD for between-treatment comparisons per day. Some data sets had missing values from animals excluded from the study due to weight loss, mortality and/or other exclusion criteria. For these data, a mixed-effects model (REML) two-way ANOVA instead of repeated measures was employed. The loss of animal numbers is represented as sample sizes having a range of values with the larger number representing initial group sizes and the smaller value representing the lowest sample sizes after animals were excluded from the study. The sample size range is provided per animal group for analyses conducted across the entire experimental timeline. Additionally, n values for multiple-mentioned groups are separated by a forward slash representing the first and second described groups, respectively. For instance, comparing 'DSS' and 'DSS+FUS' (n=6-1/7-2) denotes that the 'DSS' group had a maximum of 6 animals' data points and a minimum of 1 animal data point across all days whereas the 'DSS+FUS' group had a maximum of 7 animals' data points and a minimum of two animal data points across all days. For day-to-day analyses, comparing 'DSS' and 'DSS+FUS' on day 5 (n=4/5) denotes that the 'DSS' group had 4 data points and the 'DSS+FUS' group had 5 data points on day 5. Colon length comparisons were performed using one-way ANOVA with multiple comparisons using the Holm-Sidak post-hoc test. Data are shown as mean±standard error of mean (SEM) and statistical significance was determined at p<0.05.

Figure 3:
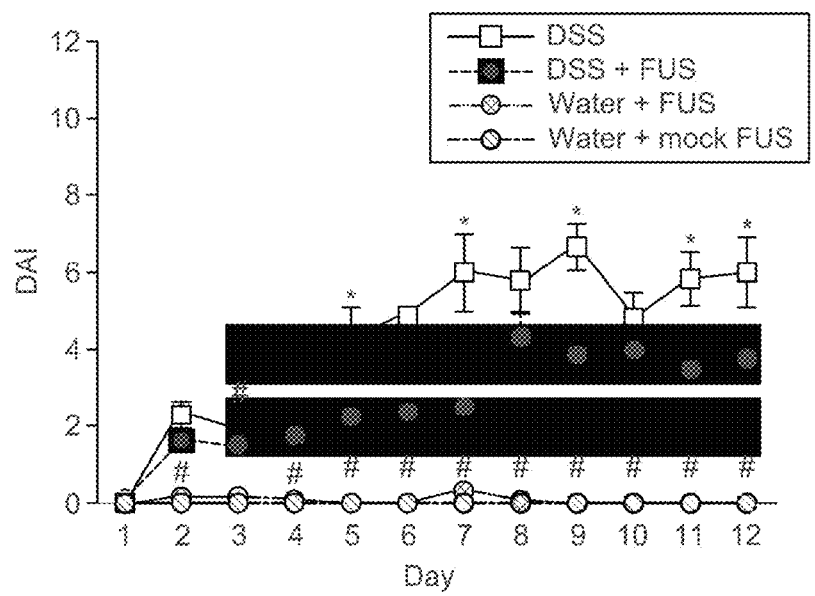
FIG. 3 shows changes in disease activity index (DAI) over the course of repeated focused ultrasound (FUS) treatments in the dextran sulfate sodium (DSS)-ingested animal model relative to control.

FIG. 3 shows DAI scores for DSS animals with or without focused ultrasound treatment. Animals either received water or DSS. Within these two groups were cohorts of animals who received focused ultrasound (FUS) MSS+FUS' and 'Water+FUS'), and those that did not ('DSS' and 'Water+mock FUS,' the latter receiving a sham ultrasound session). Rats in the 'DSS' group (n=7-1) exhibited higher DAI scores compared to animals drinking tap water (n=11-2) as soon as after one day of drinking DSS. The 'DSS+FUS' group (n=8-4) had lower DAI score, indicating less severe IBD symptomatology. Accordingly, as provided herein, focused ultrasound that targets the celiac plexus may lead to improvement in symptoms associated with IBD. The difference in DAI scores between the 'DSS' and 'DSS+FUS' groups was first significant on day 5 (n=5/4) and continued to be significant on day 7 (n=2/4), 9 (n=6/8), 11 (n=6/8), and 12 (n=4/4). Asterisks (*) denote p<0.05 for 'DSS' vs. 'DSS+FUS' whereas pound (#) denote p<0.05 for 'DSS+FUS' vs. 'Water+FUS.

The cohort in FIG. 3 represents five percent (5%) DSS, which induced significant increases in DAI scores in the 'DSS' group in comparison to the 'Water+mock FUS' control group (n=7-1/11-2; p<0.001, FIG. 3). The difference in DAI between these two groups was significant after one day of drinking DSS (n=4/11; p=0.004) until the end of the experiment on day 12 (n=4/2; p<0.001). When comparing DSS groups, those receiving focused ultrasound MSS+FUS' group) had significantly healthier DAI scores than those not receiving focused ultrasound ('DSS' group) (n=8-4/7-2; p=0.045) on day 5 (n=5/4, p=0.014), day 7 (n=2/4, p=0.047), day 9 (n=6/8, p=0.007), day 11 (n=6/8, p=0.022) and day 12 (n=4/4, P=0.022). On day 7, where maximum efficacy between the 'DSS' and 'DSS+FUS' groups was noted (n=2/4), the former had a DAI score of 6±1.4 and the latter group had a DAI score of 2.5±1.7. No difference in DAI scores was reported between 'Water+FUS' and 'Water+mock FUS' (n=11-2/5-1; p=0.222). Interestingly, although focused ultrasound was efficacious in the overall DAI score for rats drinking DSS, weight loss in the 'DSS' group (FIG. 6) was not observed, which is one of the subcategories comprising the DAI score and is oftentimes reported in other studies using 5% DSS by the end of the experimental period.

Figure 4:
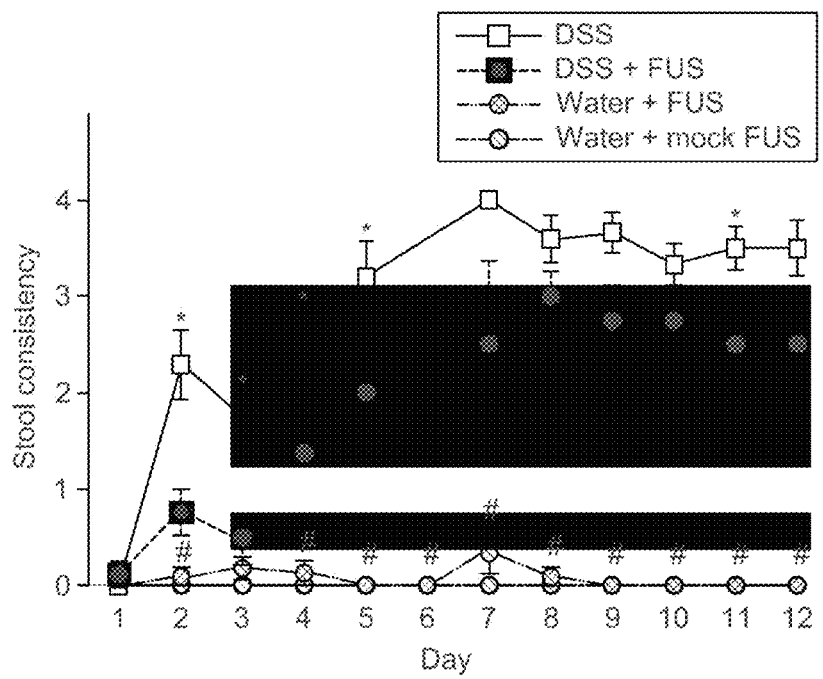
FIG. 4 shows changes in a DAI subcategory of stool consistency over the course of daily focused ultrasound treatments in the DSS-ingested animal model relative to control.
Figure 5:
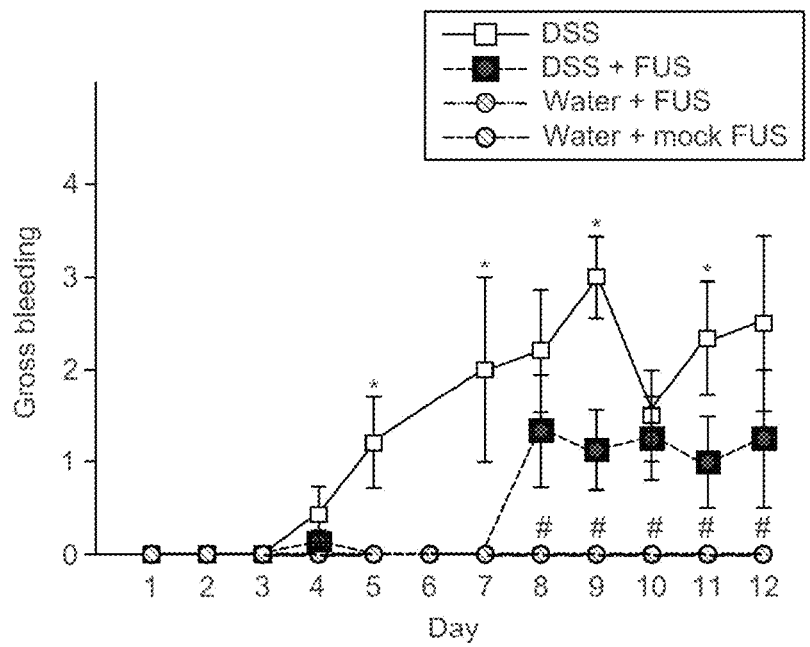
FIG. 5 shows changes in in a DAI subcategory of gross bleeding over the course of daily focused ultrasound treatments in the DSS-ingested animal model relative to control.
Figure 6:
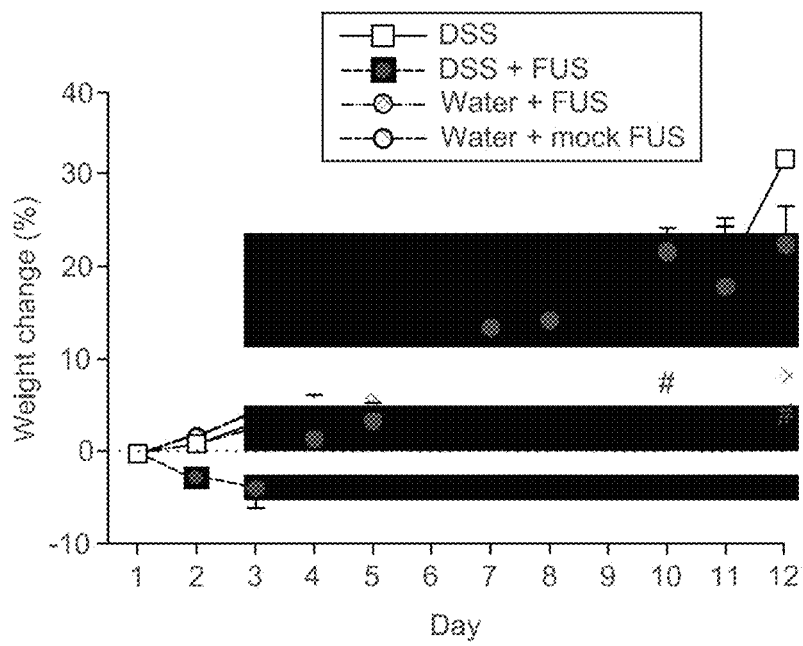
FIG. 6 shows changes in in a DAI subcategory of weight over the course of daily focused ultrasound treatments in the DSS-ingested animal model relative to control.

Each sub-category of the DAI was examined independently rather than as an aggregate index, as shown in FIGS. 4-6. Sub-categories of DAI scores comprising of stool consistency (FIG. 4), gross bleeding (FIG. 5) and weight loss (FIG. 6). In FIG. 4 animals in the 'DSS+FUS' group (n=7-2) displayed lower stool consistency scores than those in the 'DSS' group (n=8-4). This efficacy was observed as early as day 2 with continued improvements on days 3, 4, 5 and 11 in comparison to those without FUS. In FIG. 5, gross bleeding symptoms were observable in the 'DSS' group by day 5 whereas FUS delayed the emergence of gross bleeding symptoms by three days. Specifically, the 'DSS+FUS' group were no different in gross bleeding than animals in the 'Water+FUS' group until day 8. In FIG. 6, no difference was observed in weight loss between the 'DSS' and 'DSS+FUS' groups or between any other groups. Asterisks (*) denote p<0.05 for 'DSS' vs. 'DSS+FUS' whereas pound (#) denote p<0.05 for 'DSS+FUS' vs. 'Water+FUS'. DSS ingestion caused loose and runny stool consistency scores when compared to rats in the 'Water+mock FUS' and 'Water+FUS' groups (e.g., 'DSS' vs 'Water+mock FUS': n=6-1/5-1, p<0.001; 'DSS' vs 'Water+FUS': n=6-1/11-2, p<0.001). Specifically, stool consistency scores significantly worsened by day 2 and continued to have higher scores than rats drinking water with or without focused ultrasound until the end of the experiment (p<0.001 for both water group comparisons across all days, FIG. 4). Rats in the water groups, regardless of whether they received focused ultrasound or not, had similar stool consistency scores (Water+mock FUS' vs. 'Water+FUS'; p=0.113). With regards to rats in the 'DSS+FUS' group, stool consistency was significantly worse than in rats in the 'Water+FUS' group from days 4-5 and 7-12. However, rats in the 'DSS+FUS' group exhibited better stool consistency than the 'DSS' group (n=7-2/8-4; p=0.008) and specifically on day 2 (n=8/7; p<0.001), day 3 (n=4/5; p=0.006), day 4 (n=8/7; p=0.006), day 5 (n=4/5; p=0.010) and day 11 (n=8/6; p=0.036) (FIG. 4). Maximum improvement with focused ultrasound was seen on day 2 with the 'DSS' group having a stool consistency severity score of 2.2±1.0 while the 'DSS+focused ultrasound' group had a score of 0.8±0.3.

Figure 7:
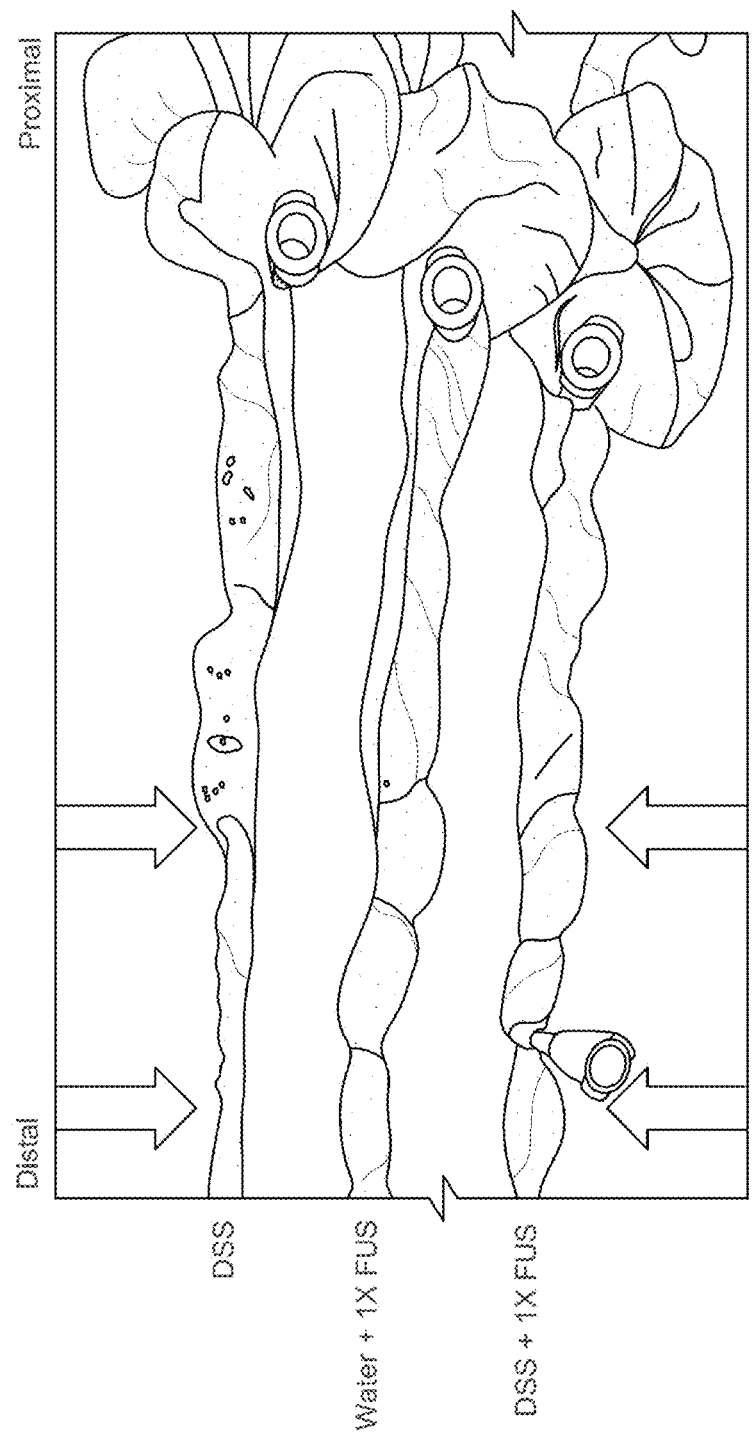
FIG. 7 is a schematic illustration of post-mortem colons of animals in the study group showing effect of DSS and focused ultrasound on stool consistency.

The effect of DSS and FUS on stool consistency can be observed in the representative image (FIG. 7) derived from a photographic image of rat colons post-mortem. Animals receiving DSS, in contrast to those in the 'Water+1×FUS' group, have colons which contain unformed pellets or lack of stool (top arrows), especially in the distal section of the colon. In contrast, animals receiving DSS and FUS MSS+1×FUS) showed intact and 'regular' pellet shape (bottom arrows) after two weeks of FUS treatment similar to those observed in the 'Water+1×FUS' group. The stool consistency scores were obtained from stool samples freshly excreted from animals in the morning each day. However, the consistency was also visually confirmable when rat colons were examined at the end of the experiment when animals were sacrificed. Then, the 'DSS+FUS' group (FIG. 7, bottom of picture) had healthier-looking tissue and harder fecal pellets more closely resembling animals drinking only tap water (FIG. 7, middle of picture) than rats in the 'DSS' group which had little shape to their stool or presence of fecal pellets (FIG. 7, top of picture).

Animals in the 'DSS' group had worse gross bleeding scores overall than the 'Water+mock FUS' animals (n=7-1/5-1; p=0.002) starting on day 5 (n=5/3; p=0.05) until day 12 (n=4/3; p=0.002) except on day 6 (n=1/1; p=0.181) (FIG. 5). Gross bleeding was similar between the 'Water+FUS' and the 'Water+mock FUS' groups throughout the 12-day period (p=1.000). Notably, animals in the 'DSS+FUS' group had significantly improved gross bleeding scores compared to those in 'DSS' group (n=7-2/8-4; p=0.015), which was first observed on day 5 (n=4/5, p=0.048), then on day 7 (n=4/2 p=0.047), day 9 (n=8/6, p=0.001) and on day 11 (n=8/6, p=0.020) (FIG. 5). Greatest improvement in gross bleeding from the 'DSS' group was seen on day 9 with the 'DSS' group having a score of 3.0±0.7 and the 'DSS+FUS' group having a score of 1.1±0.4. Moreover, the emergence of gross bleeding symptoms was delayed by approximately 3 days with focused ultrasound. Specifically, rats in the 'DSS' group exhibited a gross bleeding score of more than 1 by day 5. In contrast, the 'DSS+focused ultrasound' group first exhibited a score of more than 1 on day 8.

Although 12 days of rats drinking 5% DSS solution coincided with IBD-like symptoms such as bloody stools with loose and watery stool consistency, the hallmark symptom of weight loss in the DSS rodent model was not seen. In fact, animals drinking DSS increased their body weight despite having drank this solution daily for 2 weeks and this trend was seen in all groups ('DSS' vs. 'DSS+FUS': n=7-1/8-4, p=0.534; 'DSS+FUS' vs. 'Water+FUS': n=8-4/5-1, p=0.577; 'Water+FUS' vs. 'Water+mock FUS': n=5-1/5-1, p=0.15) FIG. 6). Interestingly, the only weight loss transiently occurred in the 'DSS+FUS' group on day 2 and 3.

Given the lack of marked and chronic weight loss, rats in the 'DSS' group only exhibited a maximum DAI score of 6.7 out of 12, which is lower than values usually reported in high-concentration rodent DSS models. In order to produce more severe IBD symptoms, a 40 kD formulation of DSS was then used instead of initial >500 kD formulation used to cause mild gastrointestinal injury above. A second set of experiments were then performed with the more potent DSS formulation to better recapitulate the severe IBD symptomatology so that assessment of FUS efficacy for this severity of IBD symptomology was possible.

Figure 8:
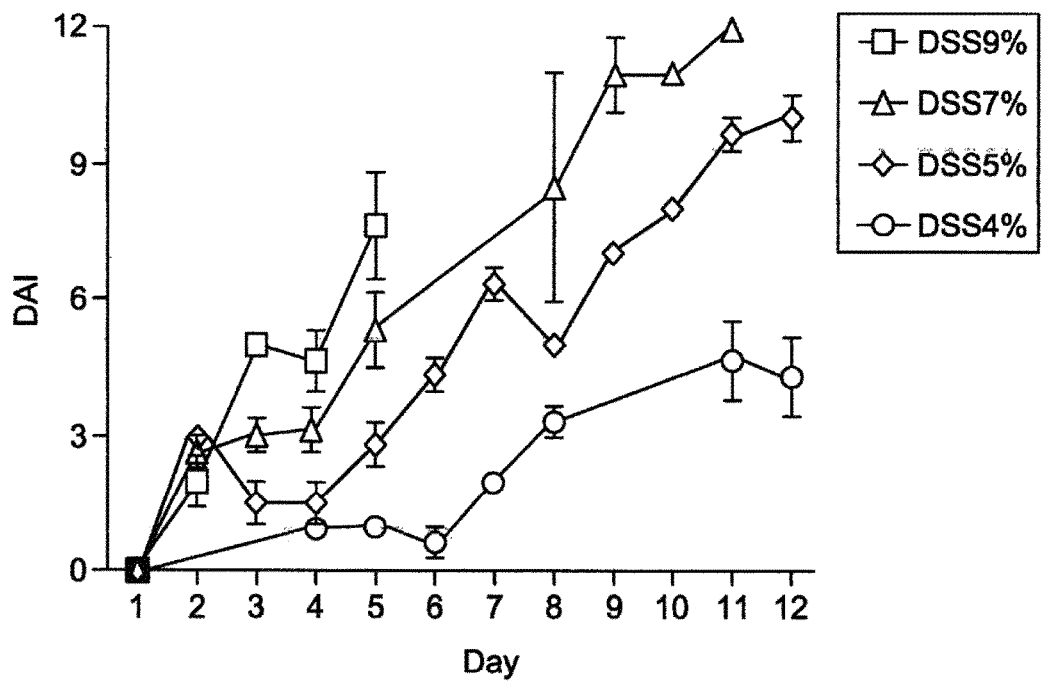
FIG. 8 shows a relationship between different concentrations of DSS on DAI scores in untreated animals.

The smaller-sized DSS chemical was investigated to determine if the model elicited an IBD symptomatology that better recapitulates severe IBD models. Different groups of rats given 4%, 5%, 7% or 9% DSS were monitored over two weeks (FIG. 8). Based on the results, 7% DSS induced the most severe IBD-like symptomology with a maximum DAI score of 12 on day 10. In contrast, 9% DSS caused high mortality and/or caused rats to be excluded from the study due to >20% weight loss by days 4-6 and 5% DSS only induced a maximum DAI score of 10. Given the optimization data, a 7% DSS concentration of the newer DSS formulation was used to investigate the efficacy of non-invasive focused ultrasound as a therapeutic for severe IBD symptomology.

Figure 15A:
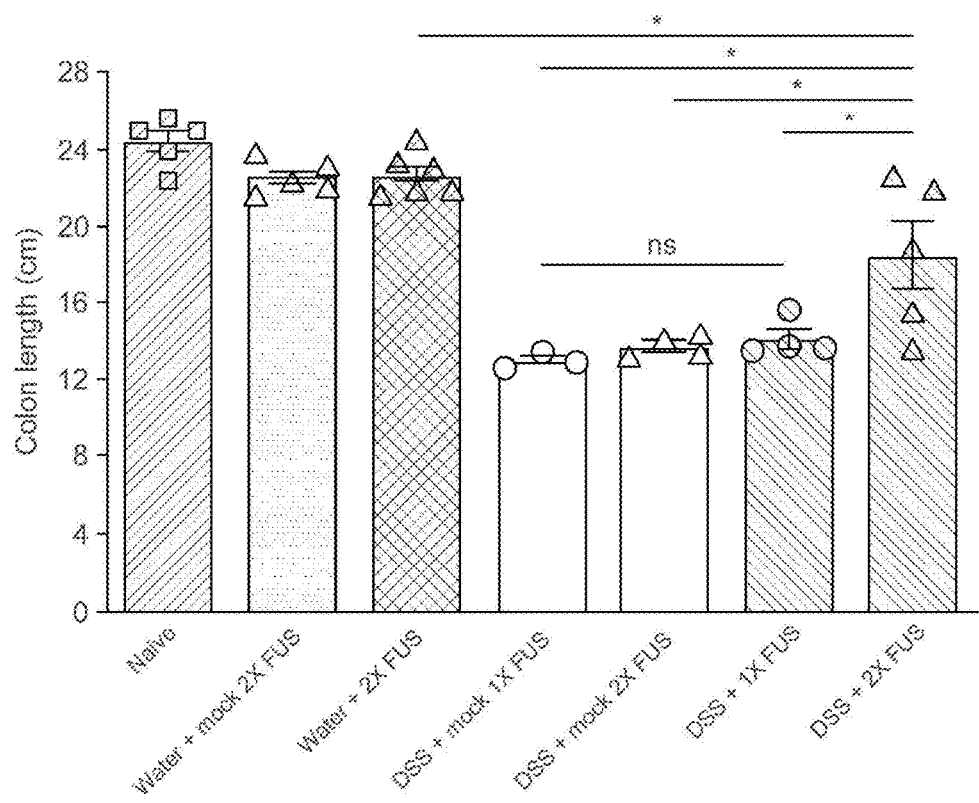
FIG. 15A shows colon lengths for various groups in the study.

To ameliorate IBD symptomatology in the 'Severe' DSS model with a 7% DSS concentration, the same focused ultrasound parameters were employed as for the 'Mild' model. However, preliminary findings revealed that DAI scores did not improve (data not shown) with animals in the 'DSS+FUS' groups having similar shortened colon lengths seen in the 'DSS' group (FIG. 15A). From the initial experiment, it was determined that a greater dosing of focused ultrasound was necessary to achieve effective enteric CAP stimulation to mitigate the increase in IBD severity. Therefore, non-invasive focused ultrasound was applied twice a day ('2×FUS') instead of once per day to provide a parallel increase in the "dosage" of the focused ultrasound therapeutic.

Figure 9:
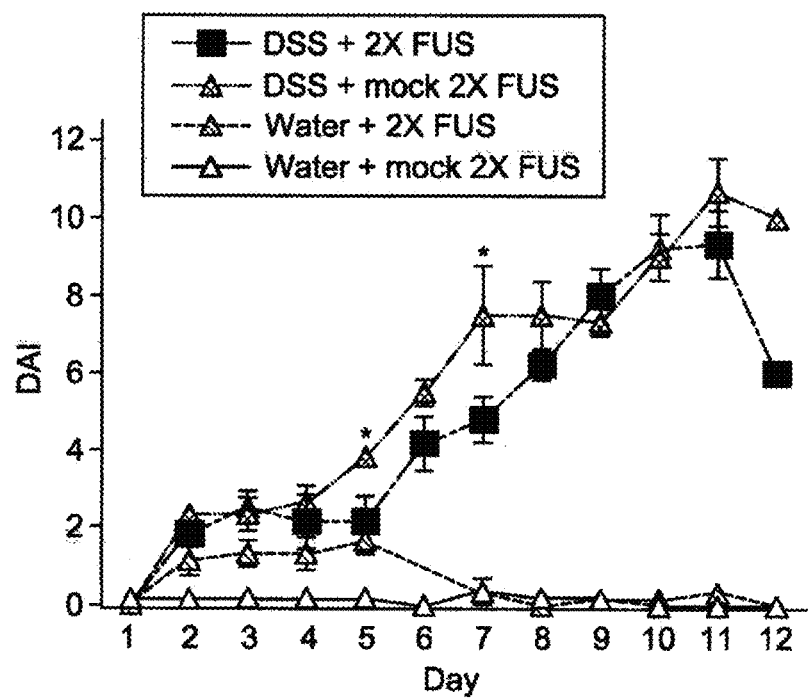
FIG. 9 shows changes in DAI over the course of twice-daily focused ultrasound treatments in DSS-ingested animal model relative to control.

FIG. 9 shows effect of 2× focused ultrasound on DAI scores in this group. Administering FUS twice daily to rats drinking DSS improved DAI symptoms in comparison to animals drinking DSS and receiving mock 2×FUS. Improvement in DAI scores were noted at day 5 (n=6/6) and again at day 7 (n=6/5). Asterisks (*) denote p<0.05 between 'DSS+2×FUS' and 'DSS+mock 2×FUS' groups. Although the 'DSS+2×FUS' group had significantly higher (worse) DAI scores than the 'Water+2×FUS' group (n=6-1/6-1; p<0.001), they were lower than those in the 'DSS+mock 2×FUS' group (n=6-1/6-1; p=0.046). Specifically, rats drinking DSS without focused ultrasound ('mock 2×FUS') had significantly higher scores than animals with DSS receiving 2× focused ultrasound by day 5 (n=6/6; p=0.037) and day 7 (7.5±1.3 vs. 4.8±0.6, n=6/5; p=0.002). Animals on day 12 may have also exhibited FUS efficacy, but sample size precluded any conclusions (10.0±0.0 vs. 6.0±0.0, n=1/1) (FIG. 9). The maximum efficacy occurred on day 7. Interestingly, no change was seen between the 'DSS+mock 2×FUS' animals and the 'DSS+2×FUS' animals on days 8, 9, 10 and 11 (p=0.11, 0.62, 0.80, 0.29, respectively), which could be due to three animals with the highest DAI scores in the 'DSS+mock 2×FUS' group excluded from the data due to mortality between days 7 (DAI: 11; 12) and 8 (DAI: 10). No animals in the 'DSS+2×FUS' group died in this time period.

Figure 10:
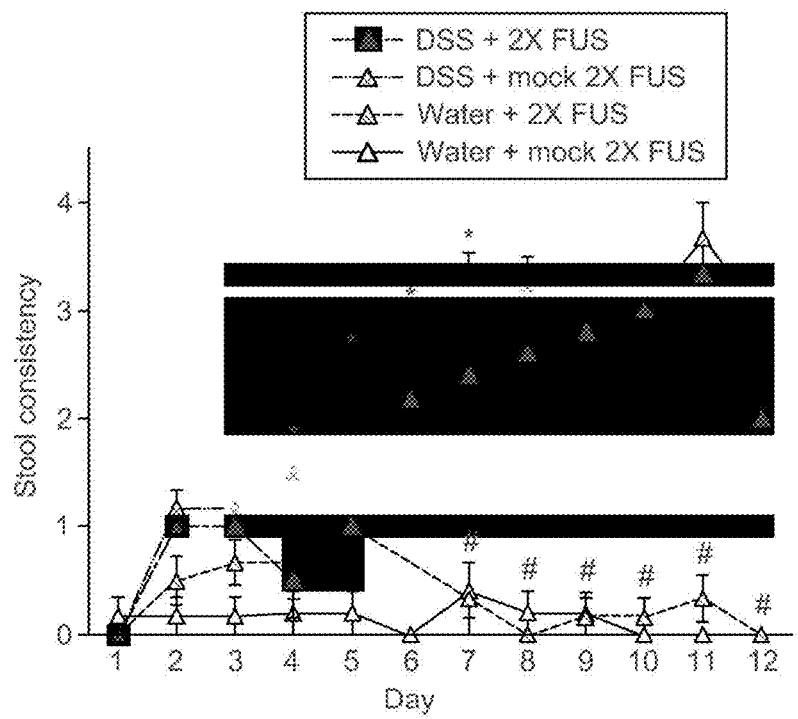
FIG. 10 shows changes in a DAI subcategory of stool consistency over the course of twice-daily focused ultrasound treatments in the DSS-ingested animal model relative to control.
Figure 11A:
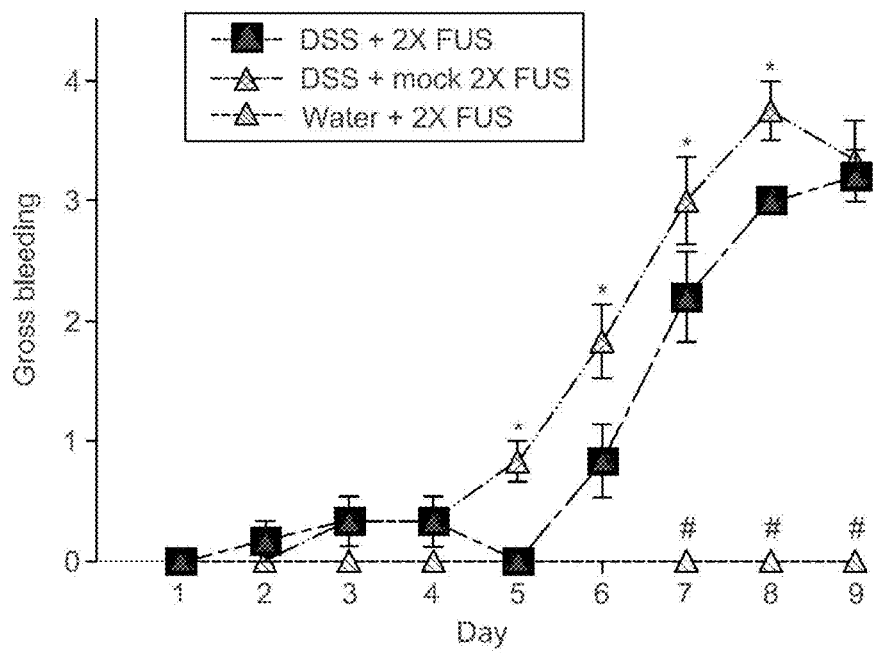
FIG. 11A shows changes in in a DAI subcategory of gross bleeding over the course of twice-daily focused ultrasound treatments in the DSS-ingested animal model relative to control.
Figure 11B:
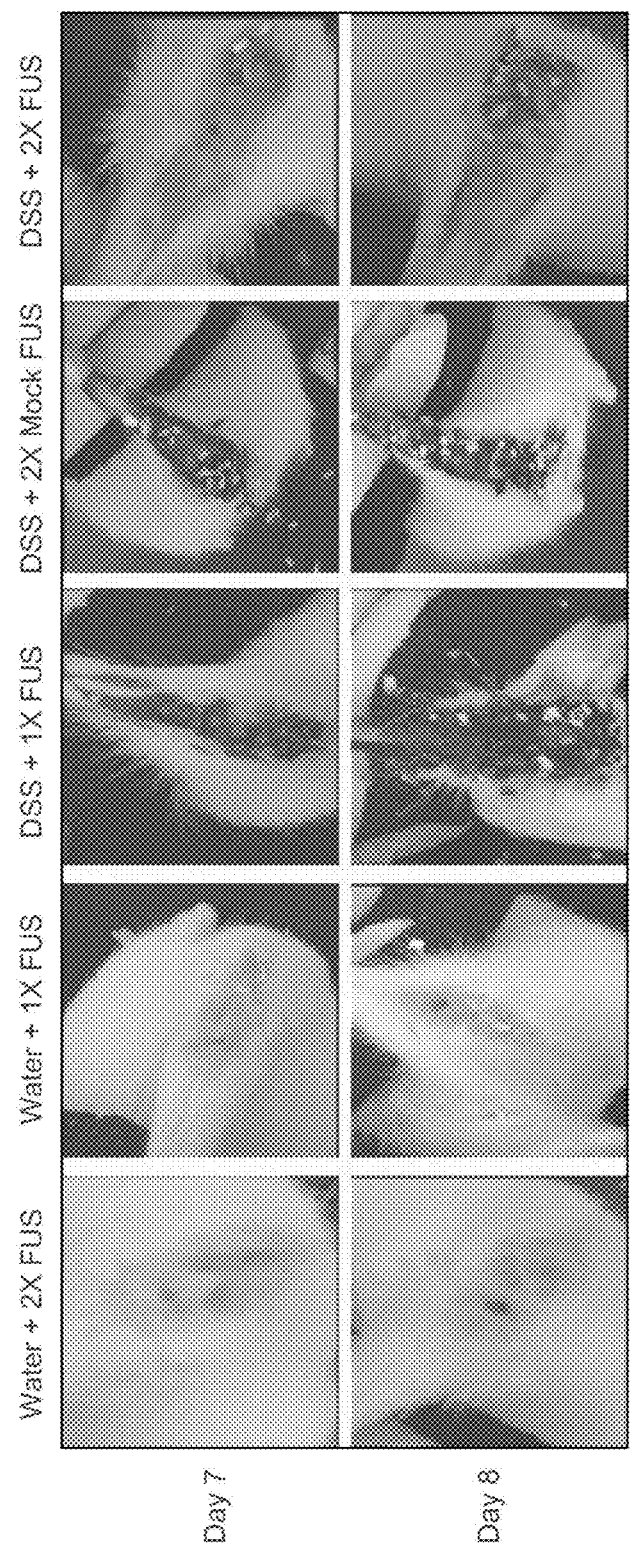
FIG. 11B shows representative photos showing changes in gross bleeding from rats on days 7 and 8 from the various treatment and control groups.
Figure 12:
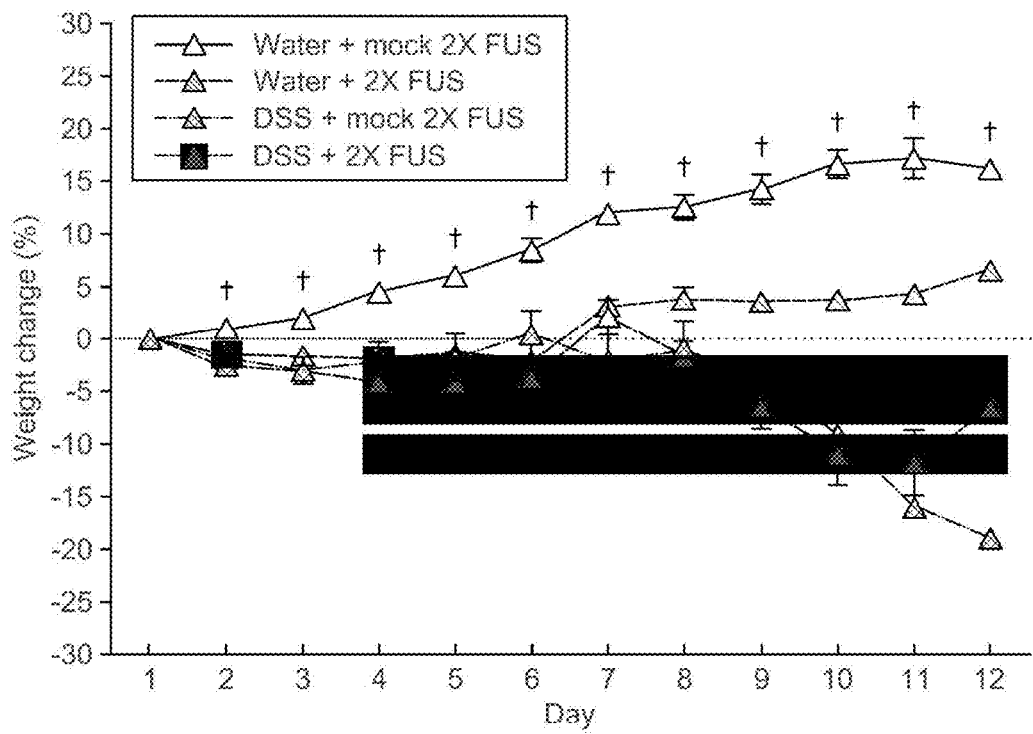
FIG. 12 shows weight changes as a percent from baseline over the course of twice-daily focused ultrasound treatments in DSS-ingested animal model relative to control.

FIGS. 10-12 show each sub-category of the DAI in detail. FIG. 10 shows effect of FUS on stool consistency scores. Animals drinking DSS and receiving 2×FUS (n=6-1) exhibited improved stool consistency when compared to those in the 'DSS+2× mock FUS' group (n=6-1). Significant improvements were noted from days 4 (n=6/6) through day 7 (n=6/5). Asterisks (*) denote p<0.05 between 'DSS+2× FUS' and 'DSS+mock 2×FUS' groups. The pound (#) denotes p<0.05 for 'DSS+2×FUS' vs. 'Water+2×FUS.' There was no difference between water-drinking animals receiving 2× focused ultrasound or 2× mock focused ultrasound (Water+2×FUS' vs 'Water+mock 2×FUS': n=6-1/6-2; p=0.068) (FIG. 10). In contrast, animals in the 'DSS+mock 2×FUS' group had worse stool consistency scores than those in the 'Water+mock 2×FUS' group (n=6-1/6-2; p<0.001), starting on day 2 (n=6/6; p<0.001) to day 12 (symbols for significance not shown). Ultrasound administered twice a day improved stool consistency in rats drinking DSS MSS+ mock 2×FUS' vs 'DSS+2×FUS': n=6-1/6-1; p<0.001) (FIG. 10), which was first observed by day 4. The latter group exhibited a stool consistency score of 0.5±0.34 while the former had a score of 1.5±0.22 (n=6/6; p=0.003). The maximum difference between groups was on day 5 with the 'DSS+mock 2× focused ultrasound' group (n=6) having a score of 2.2±0.40 and the 'DSS+2× focused ultrasound' group (n=6) having a score of 1.0±0.0 The improvement in stool consistency persisted through day 7 with the 'DSS+ 2×FUS' group possessing a stool consistency of 2.4±0.24 (n=6). In contrast, animals drinking DSS with 2× mock FUS had a score of 3.3±0.21 (n=5; p=0.008). Notably, two animals in the 'DSS+2× mock FUS' group with the highest stool consistency scores of 4 died between days 7 and 8.

FIG. 11A shows effect of FUS on gross bleeding scores. Animals drinking DSS but receiving FUS ('DSS+2×FUS'; n=6-1) had lower gross bleeding scores than those receiving mock FUS ('DSS+mock 2×FUS'; n=6-1) on day 5 (n=6/6) through 8 (n=4/5). Asterisks (*) denote p<0.05 between 'DSS+2×FUS' and 'DSS+mock 2×FUS' groups. Pound (#) denote p<0.05 for 'DSS+2×FUS' vs. 'Water+2×FUS.' FIG. 11B shows representative photos from rats on days 7 and 8 from the various treatment and control groups' Animals receiving DSS+1×FUS, as well as DSS+2× mock FUS, had darker blood due to blood stagnation within the colon from the severe disease model. In contrast, 'DSS+2×FUS' animals showed visual improvements in gross bleeding in comparison to those in the 'DSS+mock 2×FUS. The 'DSS+ mock 2×FUS' group had gross bleeding of the anus and stool whereas animals in the 'Water+2×FUS' group did not (n=6-1/6-1; p<0.001). Symptoms first emerged on day 5 (n=3/6; p=0.003), continued through day 9 (n=3/6; p<0.001) and had likely persisted until day 12 although this coincided with limited sample sizes (n=3/1) (FIG. 11A). Similar to stool consistency findings, animals in the 'DSS+2×FUS' group had reduced gross bleeding when compared to the 'DSS+2× mock FUS' group (n=6-1/6-1; p=0.012). Efficacy was first seen by day 5 (n=6/6; p=0.006) with the group receiving 2× focused ultrasound having a score of 0.0±0.0 whereas the animals drinking 7% DSS without focused ultrasound with a score of 0.83±0.31. The improved gross bleeding extended through day 8 with the 'DSS+2× mock FUS' group having a score of 3.75±0.25 and the 'DSS+2×FUS group having a score of 3.0±0.0 (n=4/5; p=0.028). Largest separation in gross bleeding scores between the two groups occurred on day 6. The 'DSS+mock 2×FUS' group exhibited a score of 2.0±0.26 whereas the 'DSS+2×FUS' group had a score of 0.83±0.30. Two animals having the most severe gross bleeding score of 4 on day 7 in the 'DSS+2× mock FUS' group died before day 8 (FIG. 11A).

FIG. 12 shows weight change as a percent from baseline with negative values representing weight loss. DSS groups with or without FUS lost weight by the end of the experiment, while water groups gained weight. No difference was observed between DSS groups receiving 2×FUS (n=6-1) or mock 2×FUS (n=6-1). The cross symbol (†) denotes p<0.05 for 'Water+mock 2×FUS' vs. 'Water+2×FUS. Rats in the 'Water+mock 2×FUS' group (n=6-2) increased their body weight over the 12-day period, but those drinking water and administered 2× focused ultrasound (n=6-3) did not gain weight at the same rate (p<0.001). In fact, the 'Water+2× FUS' group lost weight in the first 4 days of the experiment. On day 5, 'Water+mock 2×FUS' rats had gained 6.1±0.8% body weight since day 1 whereas rats in the 'Water+2×FUS' group had lost 1.4±0.5% of their body weight since day 1 (n=6/6; p<0.001). Weight loss was also seen in the 'DSS+ 2×FUS' group. However, this may largely reflect effects of 2×FUS rather than severity of IBD symptomology given that animals had firmer stool, less bleeding with little marked distress and were actively moving and displaying exploratory behaviors in their home-cages. Moreover, a similar trend in weight loss was also noted in the 'Water+2×FUS' group. Conversely, the 'DSS+mock 2×FUS' animals also lost weight (n=6-1), but they exhibited gross impairment in mobility and lethargy when handled despite having similar weight loss to animals in the 'DSS+2×FUS' group (p=0.690), FIG. 12.

Figure 13:
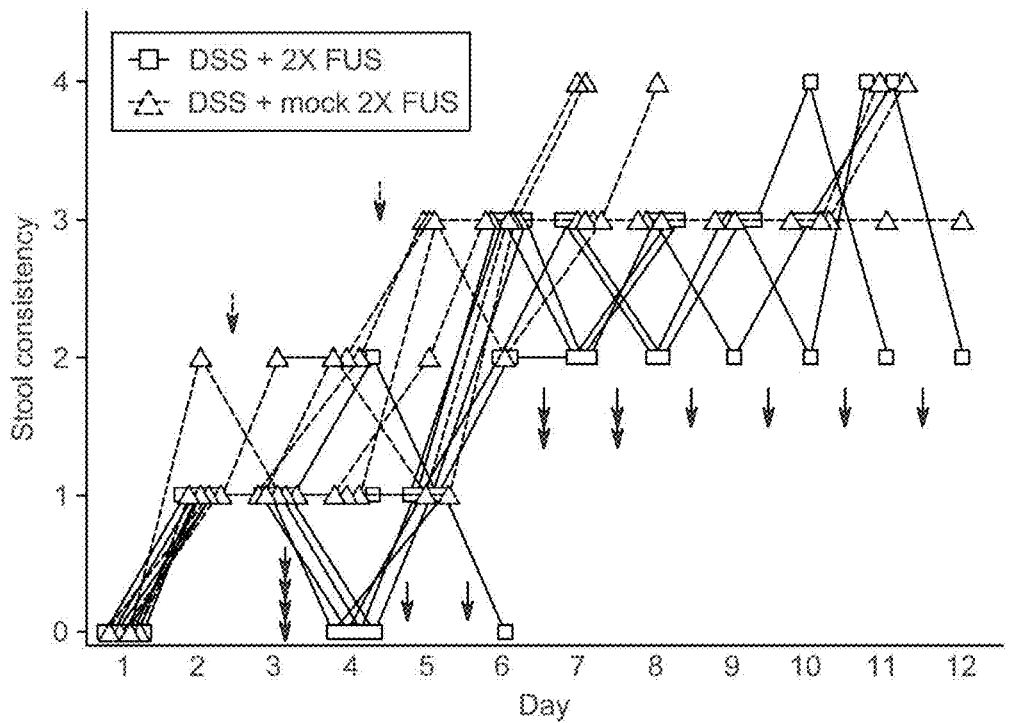
FIG. 13 shows individual animal stool consistency scores over the course of twice-daily focused ultrasound treatments in the DSS-ingested animal model relative to control.
Figure 14:
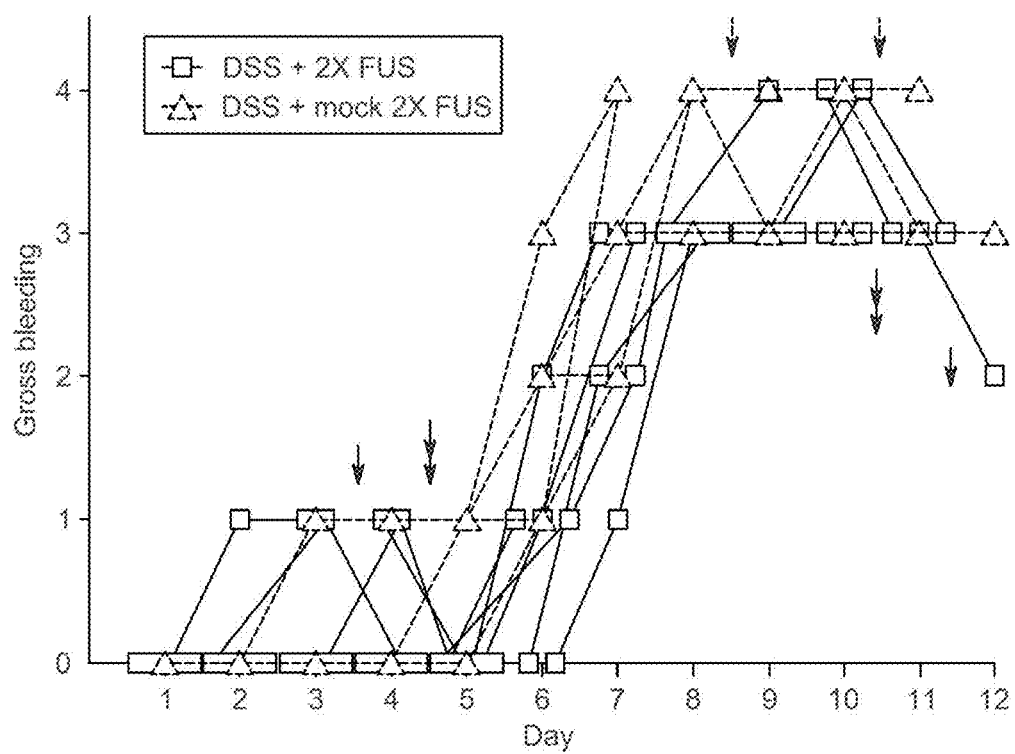
FIG. 14 shows individual animal gross bleeding scores over the course of twice-daily focused ultrasound treatments in the DSS-ingested animal model relative to control.

FIGS. 13-14 show stool consistency (FIG. 13) and gross bleeding (FIG. 14) scores for individual animals in the 'DSS+2×FUS' group (n=6-1) and the 'DSS+mock 2×FUS' group (n=6-1). Each line on the graph represents an individual animal, while each arrow next to these lines indicates a 'downturn' in score. This highlights an instance of improved symptomatology. In stool consistency scores (FIG. 13), there were 14 downturns in the 'DSS+2×FUS (n=6-1) group as shown by the number of arrows. In contrast, the 'DSS+mock 2×FUS' group (n=6-1) only had 2 downturns. FIG. 14 also shows that the 'DSS+2×FUS' animals exhibited a higher number of downturns for gross bleeding scores than the 'DSS+mock 2×FUS' animals. The scores were plotted to track changes over the 12-day period. In general, animals in the 'DSS+2×FUS' group (n=6-1) exhibited a higher number of day-to-day decreases in DAI sub-category scores than the 'DSS+mock 2×FUS' control animals (n=6-1). Specifically, rats in the 'DSS+mock 2×FUS' group exhibited sustained worsening in stool consistency severity scores with only 2 vacillations observed; one occurred between day 2 and 3 and the other between day 4 and 5 (red down-turn arrows, FIG. 13). In contrast, rats receiving ultrasound ('DSS+2×FUS') exhibited more vacillation and more day-to-day improvement in stool consistency severity with 14 vacillations (down-turn arrows) observed throughout the 12-day experiment (FIG. 13). A similar finding was seen for individual animals' gross bleeding scores (FIG. 14) with rats in the 'DSS+mock 2×FUS' group showing sustained increases (worsening) in gross bleeding symptomology except on two occasions with vacillations seen between days 8 and 9 and days 10 and 11. However, rats in the 'DSS+2×FUS' group had many instances of downward vacillations in their scores, particularly in the first half of the experiment between days 3 and 5 with three vacillations. An additional three vacillations also occurred between days 10 and 12 (FIG. 14). Analyzed across stool consistency and gross bleeding endpoints, the number of "downturns" or day-to-day improvements in severity scores were significantly higher in rats drinking DSS receiving 2× focused ultrasound than those drinking DSS with 2× mock focused ultrasound (p=0.012).

Figure 15B:
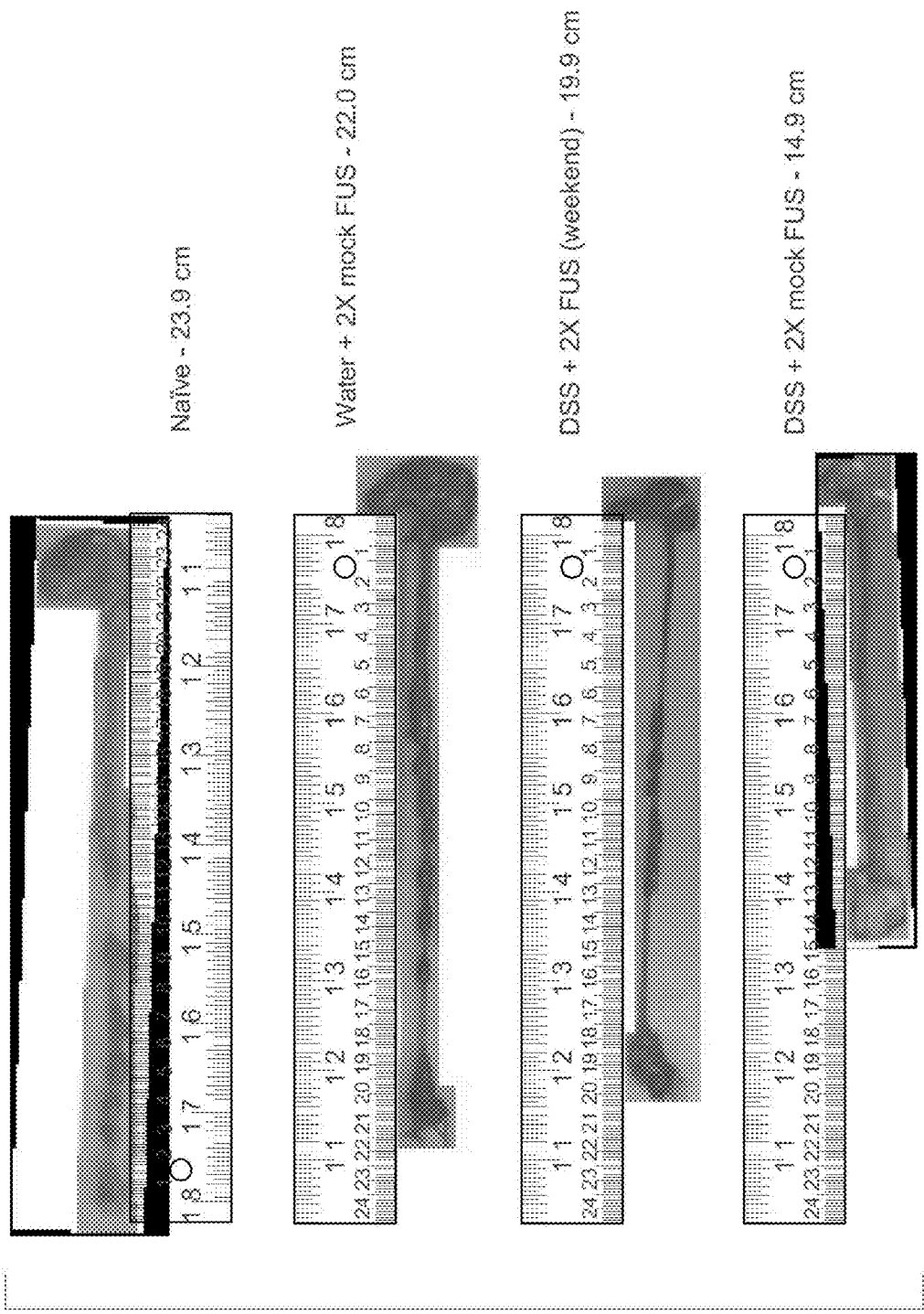
FIG. 15B shows representative photos of colon length sized relative to one another.

FIG. 15A shows group data of colon lengths. As shown on the x-axis, certain groups received water and other groups received DSS. In FIG. 15B is shown a representative pictures of group data in FIG. 15A with a ruler alongside the colon as reference. The photos are not to scale, but sized relative to each other. Pellet shape remained intact when comparing animals in the 'DSS+2×FUS' group in comparison to the 'DSS+mock 2×FUS' control group. Asterisks (*) denote p<0.05 and ns denotes no significant difference. Reduction in colon length is another important endpoint metric for DSS-induced IBD. Although the 'DSS+2×FUS' group had significantly shorter colon lengths than animals in the 'Water+2×FUS' group (p=0.016 vs.; n=5/6), it was still more intact and longer (18.5±1.8 cm) than animals in the 'DSS+mock 2×FUS' group (13.8±0.3 cm, n=5/4; p=0.013) (FIGS. 15A-B). Rats that received daily administration of focused ultrasound once a day ('DSS+1×FUS') did not improve colon lengths compared to the 'DSS+mock 1×FUS' control group with the former 14.1±0.50 cm (n=4) and the latter 13.0±0.3 cm (n=3; p=0.958). No difference in colon lengths was noted between animals in the 'Water+2×FUS' group (n=6) and the 'Water+2× mock FUS' group (n=5) with lengths of 22.7±0.5 cm and 22.6±0.4 cm, respectively (p=0.958).

Figure 16A:
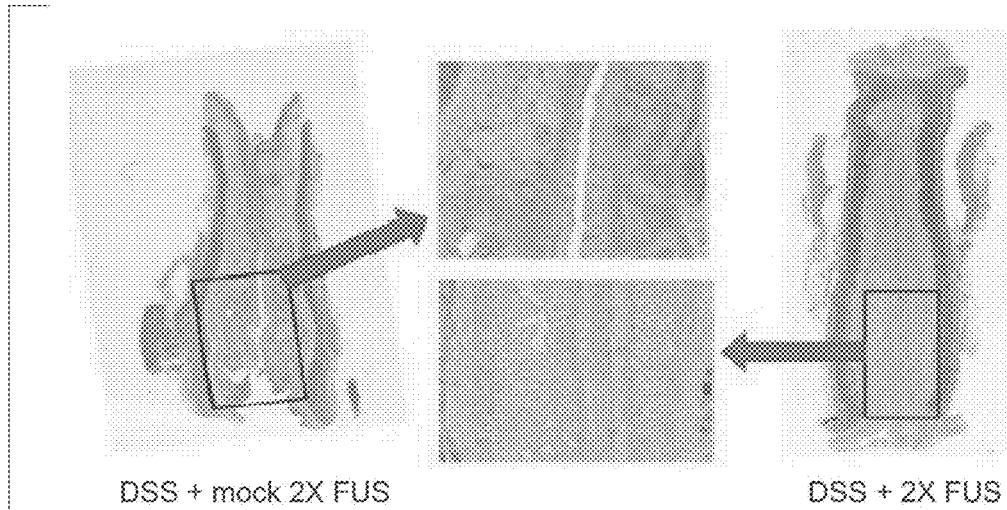
FIG. 16A shows colon hematoxylin and eosin Y stained sections of twice-daily focused ultrasound treated (DSS)-ingested animals model relative to control.
Figure 16B:
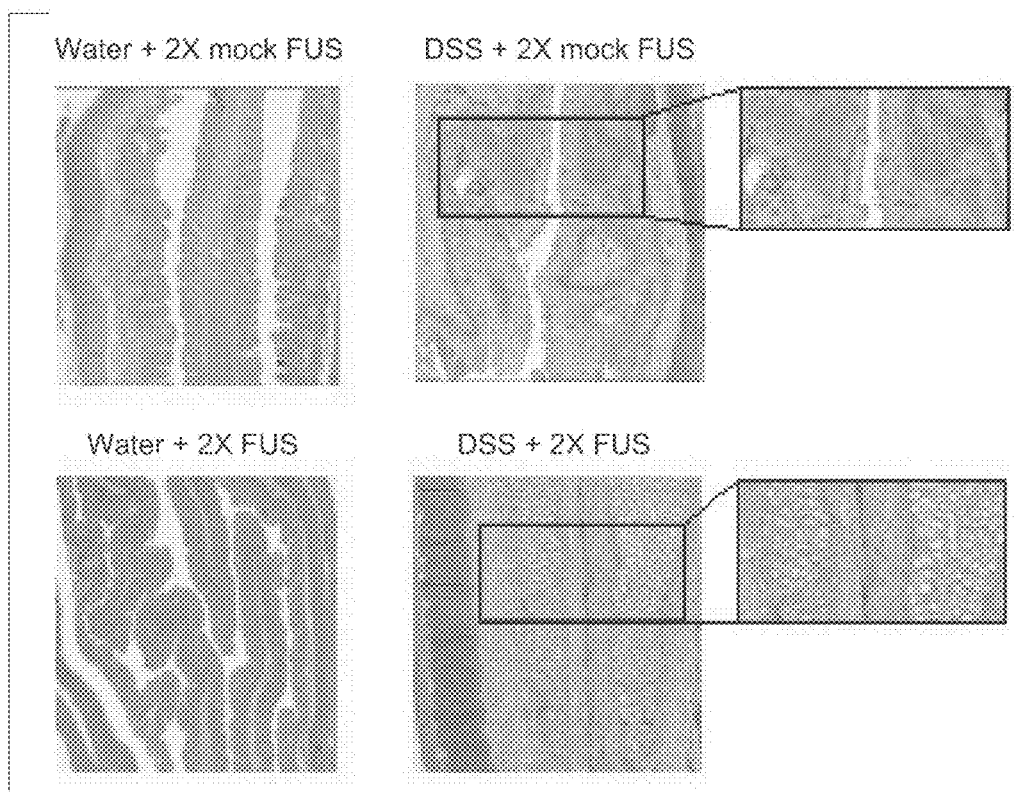
FIG. 16B shows colon hematoxylin and eosin Y stained sections of daily focused ultrasound treated (DSS)-ingested animals model relative to control.
Figure 16C:
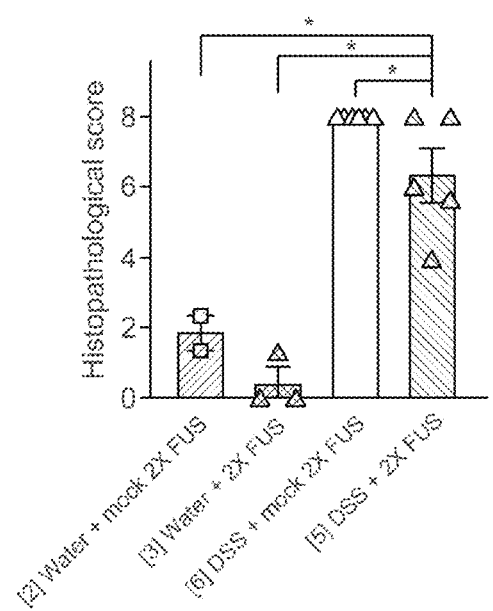
FIG. 16C shows histopathological scores for various groups in the study.

FIGS. 16A-C show histopathological data. The 2 cm of the distal section of the colon was preserved in paraformaldehyde immediately after sacrifice. The sections were processed with hematoxylin and eosin Y staining. In FIG. 16A, mucosal damage to the distal section of the colon in an animal drinking DSS with mock focused ultrasound treatment is shown (left image) compared to a DSS animal with 2× focused ultrasound (right image). There are increased lesions and infiltration of the crypt basis and deep submucosa layer. FIG. 16B shows close-up of inflammatory factors in animals receiving DSS (top right image) which is not seen in those receiving DSS+2×FUS (bottom right image). FIG. 16C is grouped data derived from scoring criteria for semi-quantitative analyzes. Colon was taken from animals in the 'Water+mock 2×FUS' (n=2), 'Water+2×FUS' (n=3), 'DSS+mock 2×FUS' (n=6) and 'DSS+2×FUS' (n=5) groups. Those in the 'DSS+mock 2×FUS' group had the highest histopathological score of 8 exhibiting maximum epithelial damage and infiltration of inflammatory cells at the end of experiment (FIG. 16B: top right image vs. bottom right image). Rats drinking DSS and receiving 2× focused ultrasound had a higher histopathological score (mean score: 6.3, SEM: 0.8) than the 'Water+2×FUS' group (mean score: 0.4, SEM: 0.4) and the 'Water+mock 2×FUS' group (mean score: 1.8, SEM: 0.5) (p<0.001). However, receiving 2× focused ultrasound while drinking 7% DSS still coincided with healthier colon than the 'DSS+mock 2×FUS' animals (mean scores: 8.0, SEM: 0.0) (p=0.022) (FIG. 13c). There was no difference between the 'Water+2×FUS' and 'Water+mock 2×FUS' groups (p=0.173) (FIG. 16C).

Figure 18:
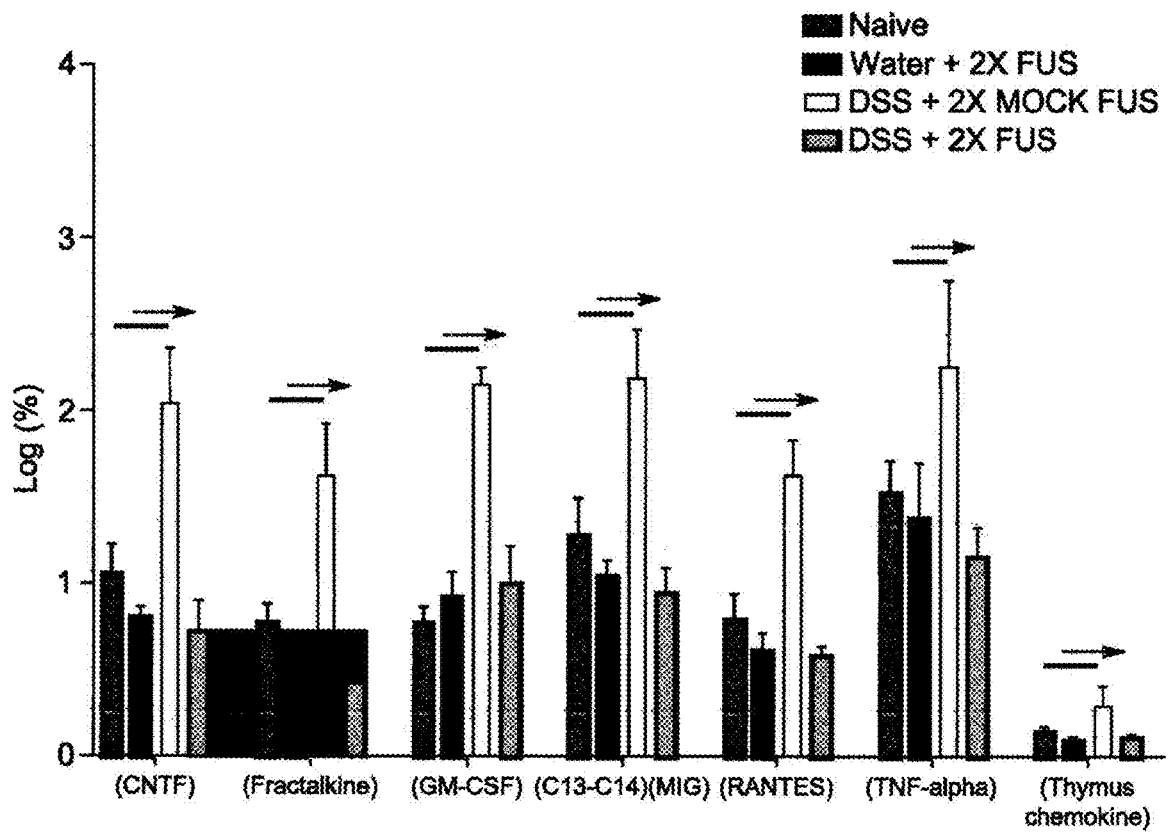
FIG. 18 shows changes in activity of individual cytokines in the animal groups from the data of FIG. 17.

Cytokine activity was assessed from the colon of rats in the "Naïve", "Water+2×FUS", "DSS+2× mock FUS" and "DSS+2×FUS" groups (n=4 rats per group). Among the 29 cytokines that were detected using a rat cytokine array (FIG. 17), seven cytokines were found with consistent results leading to significant differences between 'Naïve' vs. 'DSS+2× mock FUS'; 'Water+2×FUS' vs. 'DSS+2× mock FUS'; 'DSS+2× mock FUS' vs. 'DSS+2×FUS' (FIG. 18). Specifically, ciliary neurotrophic factor (CNTF), fractalkine, granulocyte-macrophage colony-stimulating factor (GM-CSF), monokine induced by gamma interferon (MIG), regulated on activation, normal T cell expressed and secreted (RANTES), tumor necrosis factor-alpha (TNF-alpha) and thymus chemokine all increased in rats drinking DSS with mock 2×FUS from naïve rats or those drinking water with 2×FUS. Moreover, these were all reduced to 'naïve' and 'water+2×FUS' levels in animals drinking DSS but also receiving 2×FUS (FIG. 18, bottom).

Figure 19:
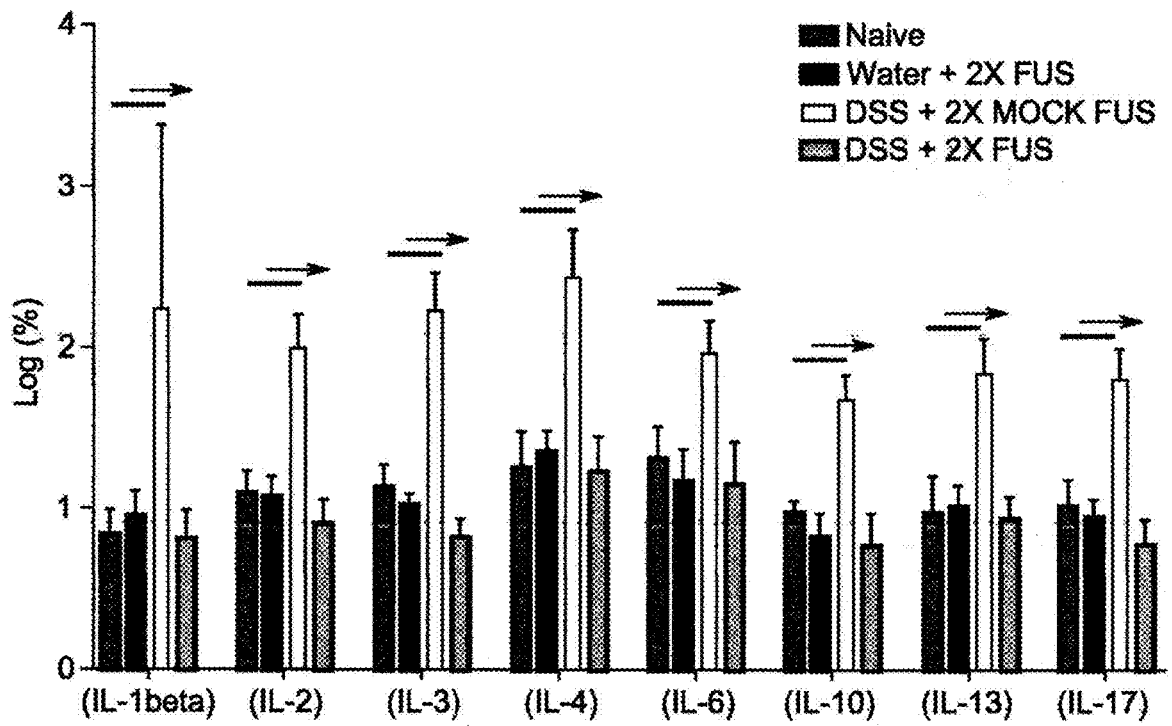
FIG. 19 shows changes in activity of individual cytokines in the animal groups from the data of FIG. 17.
Figure 20:
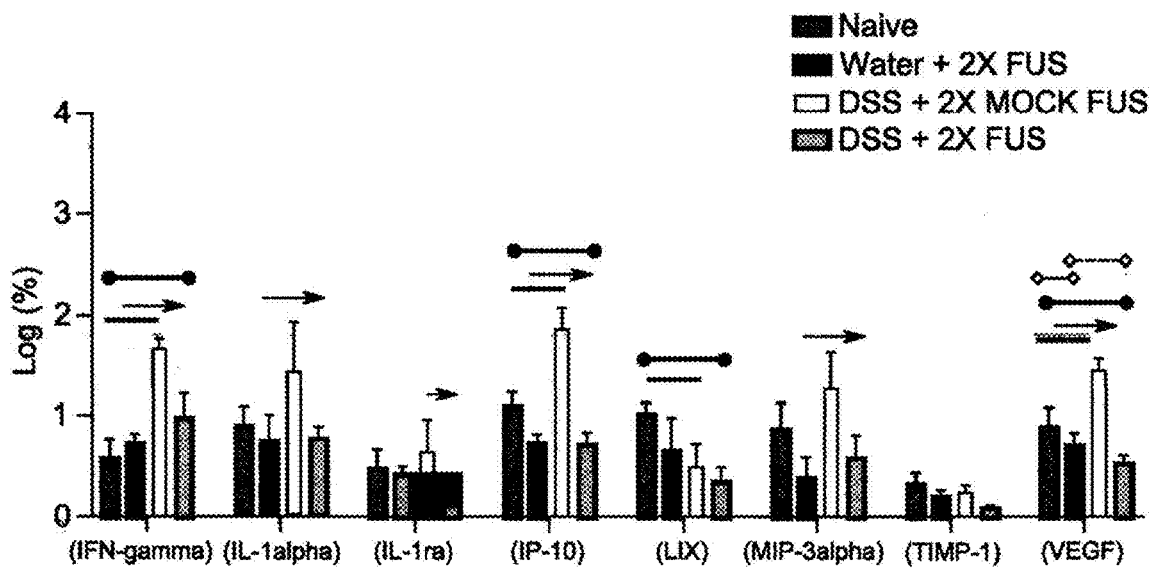
FIG. 20 shows changes in activity of individual cytokines in the animal groups from the data of FIG. 17.
Figure 21:
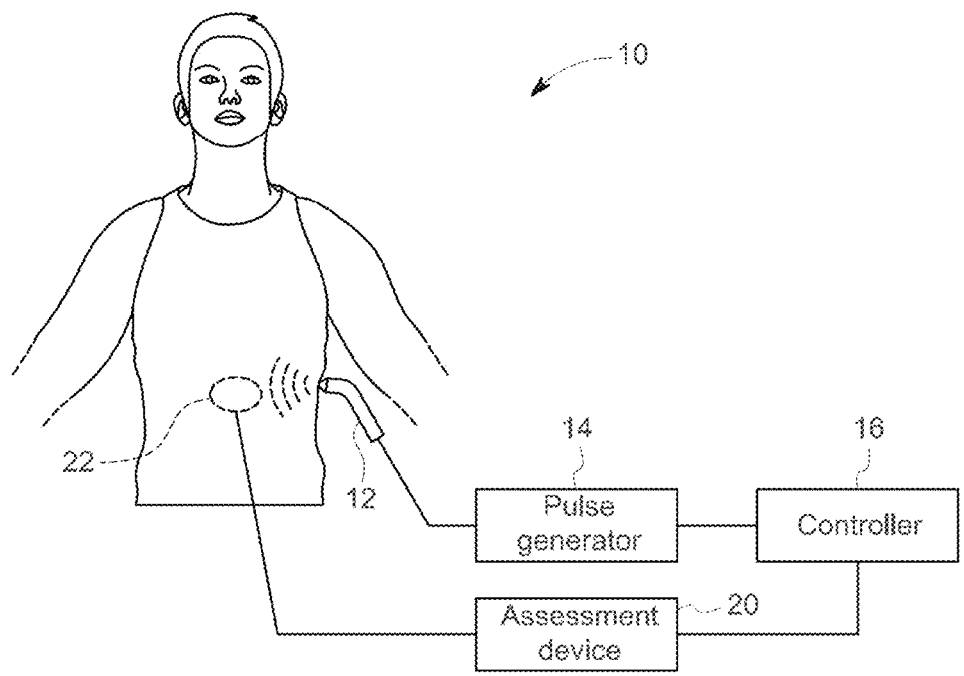
FIG. 21 is a schematic representation of a neuromodulation system according to embodiments of the disclosure.

A similar pattern of response was noted with 8 of 10 interleukin cytokines (FIG. 20) with IL-1beta, IL-2, IL-3, IL-4, IL-6, IL-10, IL-13 and IL-17 all elevated in animals drinking DSS with 2× mock FUS from 'naïve' and 'water+2×FUS' animal groups. These returned to 'naïve' and 'water+2×FUS' levels in animals drinking DSS while also receiving 2×FUS (FIG. 19, bottom). Lastly, 8 other cytokines with more variable responses to DSS and/or FUS were observed (FIG. 20). In particular, IL-1alpha and IL-1ra are 2 other interleukins in the assay kit. IL-1ra levels were not elevated in animals drinking DSS without 2×FUS from 'naïve' or 'water+2×FUS' animals whereas IL-1alpha levels were higher in 'DSS+2×FUS' animals than those in the 'water+2×FUS' animals but not from 'naïve' rats (FIG. 21, bottom). Regardless, both interleukins were reduced in animals drinking DSS with 2×FUS from those drinking DSS without 2×FUS. Interferon gamma (IFN-gamma) levels increased in animals drinking DSS without 2×FUS from 'naïve' and 'water+2×FUS' groups, but decreased with 2×FUS (FIG. 20, bottom). This reduction was still higher than levels seen in 'naïve' rats, but no different from those drinking water with 2×FUS. Not surprising, a similar pattern of change was observed for interferon gamma-induced protein 10 (IP-10, also known as CXCL10). The only cytokine that was reduced in animals drinking DSS without 2×FUS from 'naïve' rats was LIX (also known as CXCL5). Levels were unaffected with 2×FUS.

Lastly, 7 cytokines remained unchanged between all four animal groups regardless of drinking water or DSS with and without 2×FUS; this included tissue inhibitor of metalloproteinases (TIMP-1) (FIG. 20, bottom) along with cytokine-induced neutrophil chemoattractant-1 (CINC-1), CINIC2alpha/beta, CINC-3, macrophage inflammatory protein-1alpha (MIP-1alpha), soluble intercellular adhesion molecule-1 (sICAM-1) and L-Selectin (data not shown).

The disclosed neuromodulation techniques may be used in conjunction with a neuromodulation system. FIG. 21 is a schematic representation of a system 10 for neuromodulation to achieve neurotransmitter release and/or activate components (e.g., the presynaptic cell, the postsynaptic cell) of one or more synapses in a ganglion of a celiac plexus response to an application of energy. For example, one of more synapses in a ganglion of a celiac plexus may be modulated using focused ultrasound. The depicted system includes a pulse generator 14 coupled to an energy application device 12 (e.g., an ultrasound transducer). The energy application device 12 is configured to receive energy pulses, e.g., via leads or wireless connection, that in use are directed to a region of interest of an internal tissue or an organ of a subject, which in turn results in a targeted physiological outcome. In certain embodiments, the pulse generator 14 and/or the energy application device 12 may be implanted at a biocompatible site (e.g., the abdomen), and the lead or leads couple the energy application device 12 and the pulse generator 14 internally. For example, the energy application device 12 may be a MEMS transducer, such as a capacitive micromachined ultrasound transducer.

In certain embodiments, the energy application device 12 and/or the pulse generator 14 may communicate wirelessly, for example with a controller 16 that may in turn provide instructions to the pulse generator 14. In other embodiments, the pulse generator 14 may be an extracorporeal device, e.g., may operate to apply energy transdermally or in a noninvasive manner from a position outside of a subject's body, and may, in certain embodiments, be integrated within the controller 16. In embodiments in which the pulse generator 14 is extracorporeal, the energy application device 12 may be operated by a caregiver and positioned at a spot on or above a subject's skin such that the energy pulses are delivered transdermally to a desired internal tissue. Once positioned to apply energy pulses to the desired site, the system 10 may initiate neuromodulation to achieve targeted physiological outcome or clinical effects.

In certain embodiments, the system 10 may include an assessment device 20 that is coupled to the controller 16 and assesses characteristics that are indicative of whether the targeted physiological outcome of the modulation have been achieved. In one embodiment, the targeted physiological outcome may be local. For example, the modulation may result in local tissue or function changes, such as tissue structure changes, local change of concentration of certain molecules, tissue displacement, increased fluid movement, etc.

The modulation may result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 20 may be configured to assess concentration changes in some embodiments. In some embodiments, the assessment device 20 may be an imaging device configured to assess changes in organ size and/or position. While the depicted elements of the system 10 are shown separately, it should be understood that some or all of the elements may be combined with one another. Further, some or all of the elements may communicate in a wired or wireless manner with one another.

Based on the assessment, the modulation parameters of the controller 16 may be altered. For example, if a desired modulation is associated with a change in concentration (circulating concentration or tissue concentration of one or more molecules) within a defined time window (e.g., 5 minutes, 30 minutes after a procedure of energy application starts) or relative to a baseline at the start of a procedure, a change of the modulation parameters such as pulse frequency or other parameters may be desired, which in turn may be provided to the controller 16, either by an operator or via an automatic feedback loop, for defining or adjusting the energy application parameters or modulation parameters of the pulse generator 14.

The system 10 as provided herein may provide energy pulses according to various modulation parameters and as part of a treatment protocol. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. The treatment protocol duration may last for various time periods, including, but not limited to, from a few minutes to several hours. In certain embodiments, treatment duration with a specified stimulation pattern may last for one hour, repeated at, e.g., 72 hour intervals. In certain embodiments, treatment may be delivered at a higher frequency, say every three hours, for shorter durations, for example, 30 minutes. The application of energy, in accordance with modulation parameters, such as the treatment duration and frequency, may be adjustably controlled to achieve a desired result.

The focused ultrasound energy may be focused on a region of interest 22, which may be an internal structure, tissue, or an organ that includes at least a portion of the celiac plexus. For example, the region of interest may include a ganglion or ganglia of the celiac plexus. The synapses within the region of interest 22 may be stimulated by direct application of energy to the to the synapses within a field of focus of the energy application device 12 focused on the region of interest 22 of the target tissue to cause release of molecules into the synaptic space and/or the change in ion channel activity that in turn causes downstream effects such as activation of the enteric CAP. The region of interest 22 may be selected to include a particular ganglion of the celiac plexus while excluding a different ganglion of the celiac plexus (and also excluding ganglia that are not part of the celiac plexus). Accordingly, the region of interest 22 may be selected to correspond to a portion of the target tissue with or adjacent to the desired ganglion or ganglia. The energy application may be selected to preferentially trigger a release of one or more molecules such as neurotransmitters from the nerve within the synapse.

In one embodiment, energy may be applied to two or more regions of interest 22. In some embodiments, the energy application parameters may be chosen to induce preferential activation of either neural or non-neuronal components within the tissue directly receiving energy to induce a desired combined physiological effect. In certain embodiments, the energy may be focused or concentrated within a volume of less than about 25 $mm^3$. In certain embodiments, the energy may be focused or concentrated within a volume of about 0.5 $mm^3$-50 $mm^3$. A focal volume and a focal depth for focusing or concentrating the energy within the region of interest 22 may be influenced by the size/configuration of the energy application device 12. The focal volume of the energy application may be defined by the field of focus of the energy application device 12.

As provided herein, the energy may be substantially applied only to the region or regions of interest 22 to preferentially activate the synapse in a targeted manner to achieve targeted physiological outcomes and is not substantially applied in a general or a nonspecific manner across the entire tissue. Accordingly, only a subset of a plurality of different types of ganglia is exposed to the direct energy application. For example, the regions of interest within organs containing either blood vessels, nerves, or other anatomical landmarks may be spatially selected and used to identify areas with specific axon terminals and synapses. In one embodiment, the region of interest is selected by identifying a splenic or hepatic artery and spatially selecting an area close to or parallel to the splenic or hepatic artery. Organ architectures may be segmented based on sub-organ tissue function, blood vessel, and neural innervation, and subsets of axon terminals may be selected to be included in a region of interest to which energy is directly applied. Other ganglia or nerve structures may be outside of the region of interest 22 and may not be exposed to the direct applied energy. The region of interest 22 may be selected based on factors including, but not limited to, historical or experimental data (e.g., data showing an association of a particular location with a desired or targeted physiological outcome). Alternatively or additionally, the system 10 may apply energy to individual ganglia of the celiac plexus until the desired targeted physiological effect is achieved.

Figure 22:
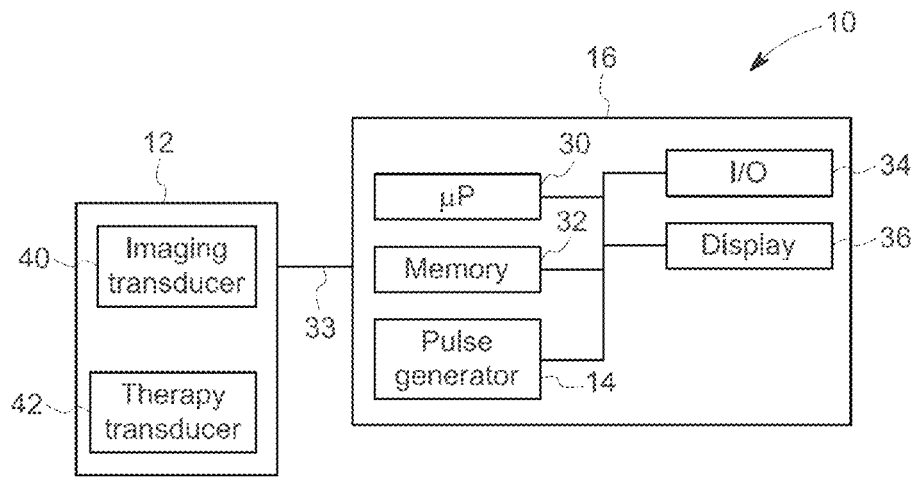
FIG. 22 is a block diagram of a neuromodulation system according to embodiments of the disclosure.

FIG. 22 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 30 for controlling the device. Software code or instructions are stored in memory 32 of the controller 16 for execution by the processor 30 to control the various components of the device. The controller 16 and/or the pulse generator 14 may be connected to the energy application device 12 via one or more leads 33 or wirelessly The controller 16 also includes a user interface with input/output circuitry 34 and a display 36 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to the control signals from controller device 16 to vary the stimulation characteristics of energy pulses transmitted through lead 33 to an subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 16 permits adjustably controlling the energy by changing the modulation parameters and/or initiating energy application at certain times or cancelling/suppressing energy application at certain times. In one embodiment, the adjustable control of the energy application device is based on information about a concentration of one or more molecules in the subject (e.g., a circulating molecule, such as a biomarker associated with IBD). If the information is from the assessment device 20, a feedback loop may drive the adjustable control. For example, if a circulating IBD biomarker concentration, as measured by the assessment device 20, is above a predetermined threshold or range, the controller 16 may initiate energy application to a region of interest and with modulation parameters that are associated with a reduction in the biomarker. The initiation of energy application may be triggered by the IBD biomarker drifting above a predetermined (e.g., desired) threshold or outside a predefined range. In another embodiment, the adjustable control may be in the form of altering modulation parameters when an initial application of energy does not result in an expected change in a targeted physiological outcome (e.g., concentration of a molecule of interest) within a predetermined time frame (e.g., 1 hour, 2 hours, 4 hours, 1 day).

In one embodiment, the memory 32 stores different operating modes that are selectable by the operator. For example, the stored operating modes may include instructions for executing a set of modulation parameters associated with a particular treatment site. Different sites may have different associated modulation parameters. Rather than having the operator manually input the modes, the controller 16 may be configured to execute the appropriate instruction based on the selection. In another embodiment, the memory 32 stores operating modes for different types of treatment. For example, activation may be associated with a different stimulating pressure or frequency range relative to those associated with depressing or blocking tissue function. In a specific example, when the energy application device is an ultrasound transducer, the time-averaged power (temporal average intensity) and peak positive pressure are in the range of 1 $mW/cm^2$-30,000 $mW/cm^2$ (temporal average intensity) and 0.1 MPa to 7 MPa (peak pressure). In one example, the temporal average intensity is less than 35 $W/cm^2$ in the region of interest to avoid levels associated with thermal damage & ablation/cavitation. In another specific example, when the energy application device is a mechanical actuator, the amplitude of vibration is in the range of 0.1 to 10 mm. The selected frequencies may depend on the mode of energy application, e.g., ultrasound or mechanical actuator.

In another embodiment, the memory 32 stores a calibration or setting mode that permits adjustment or modification of the modulation parameters to achieve a desired result. In one example, the stimulation starts at a lower energy parameter and increases incrementally, either automatically or upon receipt of an operator input. In this manner, the operator may achieve tuning of the induced effects as the modulation parameters are being changed.

The system may also include an imaging device, such as imaging transducer 40 that facilitates focusing the energy application device 12 by acquiring imaging data when the energy application device 12 is operating in an imaging mode under instructions from the controller 16. The energy application device 12 may include an ultrasound therapy transducer 42 that is capable of applying focused ultrasound energy to a target that is within the region of interest 22 when operating in a therapy mode under instructions from the controller 16. The energy application device 12 may include control circuitry for controlling the imaging transducer 40 and/or the ultrasound therapy transducer 42. The control circuitry of the processor 30 may be integral to the energy application device 12 (e.g., via an integrated controller 16) or may be a separate component. The imaging transducer 40 may also be configured to acquire image data to assist with spatially selecting a desired or targeted region of interest and focusing the applied energy on the region of interest of the target tissue or structure.

In one embodiment, the imaging device (transducer 40) may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 32 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. In one embodiment, the controller 16 may be programmed to automatically identify or select the region of interest based on the image data. In an embodiment, the image data may be displayed on the display 36, and an operator may designate portions of the image that correspond to the region of interest. Based in the user input, the controller 16 may select the region of interest. Based on the spatial selection, the energy application device 12 may be focused on the selected volume corresponding to the region of interest. For example, the energy application device 12 may be configured to first operate in the imaging mode to apply imaging mode energy that is used to capture image data to be used for identifying the region of interest. The imaging mode energy is not at levels and/or applied with modulation parameters suitable for preferential activation. However, once the region of interest is identified, the controller 16 may then operate in a treatment mode according to the modulation parameters associated with neuromodulation as provided herein.

The controller 16 may also be configured to receive inputs related to the targeted physiological outcomes as an input to the selection of the modulation parameters. For example, when an imaging modality is used to assess a tissue characteristic, the controller 16 may be configured to receive a calculated index or parameter of the characteristic. Based on whether the index or parameter is above or below a predefined threshold, the modulation parameters may be modified. In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 may operate under control of the controller 16 to a) acquire image data of a tissue that may be used to spatially select a region of interest within the target tissue b) apply the modulating energy to the region of interest and c) acquire image data to determine that the targeted physiological outcome has occurred (e.g., via displacement measurement). In such an embodiment, the imaging device, the assessment device 20 and the energy application device 12 may be the same device.

In another implementation, a desired modulation parameter set may also be stored by the controller 16. In this manner, subject-specific parameters may be determined. Further, the effectiveness of such parameters may be assessed over time. If a particular set of parameters is less effective over time, the subject may be developing insensitivity to activated pathways. If the system 10 includes an assessment device 20, the assessment device 20 may provide feedback to the controller 16. In certain embodiments, the feedback may be received from a user or an assessment device 20 indicative of a characteristic of the target physiological outcome. The controller 16 may be configured to cause the energy application device to apply the energy according to modulation parameters and to dynamically adjust the modulation parameters based on the feedback. For example, based on the feedback, the processor 16 may automatically alter the modulation parameters (e.g., the frequency, amplitude, or pulse width of an ultrasound beam or mechanical vibration) in real time and responsive to feedback from the assessment device 20.

The disclosed techniques may be used in assessment of neuromodulation effects, which in turn may be used as an input or a feedback for selecting or modifying neuromodulation parameters. The disclosed techniques may use direct assessments of tissue condition or function as the targeted physiological outcomes. The assessment may occur before (i.e., baseline assessment), during, and/or after the neuromodulation.

The assessment techniques may include at least one of functional magnetic resonance imaging, diffusion tensor magnetic resonance imaging, positive emission tomography, or acoustic monitoring, thermal monitoring. The assessment techniques may also include protein and/or marker concentration assessment. The images from the assessment techniques may be received by the system for automatic or manual assessment. Based on the image data, the modulation parameters may also be modified. For example, a change in organ size or displacement may be utilized as a marker of local neurotransmitter concentration, and used as a surrogate marker for exposure of local cells to phenotype modulating neurotransmitters, and effectively as a marker of predicted effect on IBD pathways. The local concentration may refer to a concentration within a field of focus of the energy application.

Additionally or alternatively, the system may assess the presence or concentration of one or more molecules in the tissue or circulating in the blood. The concentration in the tissue may be referred to as a local concentration or resident concentration. Tissue may be acquired by a fine needle aspirate, and the assessment of the presence or levels of molecules of interest (e.g., metabolic molecules, markers of metabolic pathways, peptide transmitters, catecholamines) may be performed by any suitable technique known to one of ordinary skilled in the art. As provided herein, the molecule of interest may be one or more of an IBD biomarker, which may be a cytokine (TNF-alpha, IL-1 beta), perinuclear anti-neutrophil antibody, anti-*Saccharomyces Cerevisiae* antibody, calprotectin, C-reactive protein, or anti-flagellin antibody.

In other embodiments, the targeted physiological outcomes may include, but are not limited to, tissue displacement, tissue size changes, a change in concentration of one or more molecules (either local, non-local, or circulating concentration), a change in gene or marker expression, afferent activity, and cell migration, etc. For example, tissue displacement (e.g., a blood vessel displacement of an adjacent artery) may occur as a result of energy application to the tissue. By assessing the tissue displacement (e.g., via imaging), other effects may be estimated. For example, a certain displacement may be characteristic of a particular change in molecule concentration.

Figure 23:
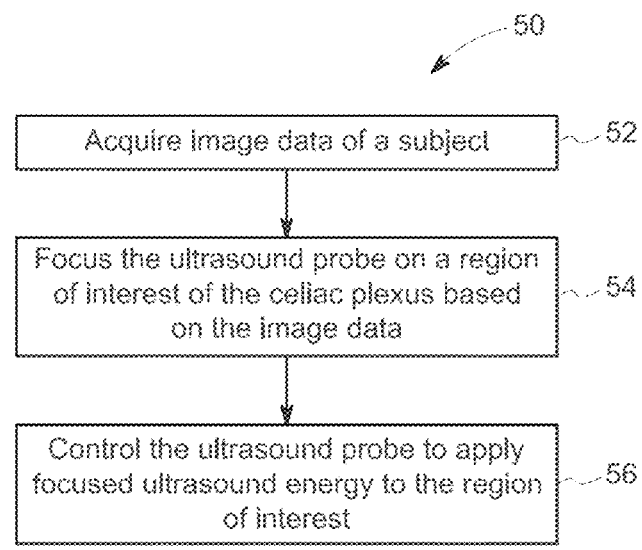
FIG. 23 is a flow diagram of a method of neuromodulation according to embodiments of the disclosure.

FIG. 23 is a flow diagram of a method 50 for neuromodulation of a celiac plexus. In the method 50, image data of the subject is acquired at step 52 to identify the region of the subject likely to include the desired peripheral ganglion to be modulated. For example, while an individual ganglion may be challenging to visualize using ultrasound images, identification of one or more visualized anatomical landmarks may be used to identify the region of interest. Such visual landmarks may include identification of an abdominal aorta and one or more junction points with arteries adjacent to peripheral ganglia of the celiac plexus. In one example, the region of interest may be positioned to include a junction of the abdominal aorta with a hepatic artery or with a splenic artery. In another example, the region of interest may be selected based on a relative position to (e.g., 1-10 mm spaced apart from) such a junction. The energy application device is positioned such that the energy pulses are focused at the desired region of interest at step 54, and the pulse generator applies a plurality of energy pulses to the region of interest of the target tissue at step 56 to preferentially activate at least a portion of a peripheral ganglion located in the celiac plexus that is positioned in the region of interest, e.g., to stimulate the ganglion to release neurotransmitters and/or induce altered neurotransmitter release and/or induce altered activity as provided herein. In an embodiment, the region of interest comprises a celiac plexus or at least a portion of a celiac plexus. In an embodiment, the region of interest comprises a peripheral ganglion of a celiac plexus. In certain embodiments, the method may include a step of assessing the effect of the stimulation. For example, one or more direct or indirect assessments of a state of tissue function or condition may be used. Based on the tissue function as assessed, the modulation parameters of the one or more energy pulses may be modified (e.g., dynamically or adjustably controlled) to achieve the targeted physiological outcome.

In one embodiment, assessments may be performed before and after applying energy pulses to assess a change in concentration of a molecule of interest, a stool characteristic (stool consistency, stool blood presence). In one embodiment, the assessment may include a DAI determination. If the assessment marker is above or below a threshold, appropriate modification in the modulation parameters may be made. For example, if the marker is within or associated with a desired physiological outcome, the energy applied during neuromodulation may be stepped back to a minimum level that supports the desired outcome. If the change in the characteristic relative to the threshold is associated with insufficient change in marker, certain modulation parameters, including, but not limited to, the modulation amplitude or frequency, the pulse shape, the stimulation pattern, and/or the stimulation location may be changed.

Further, the assessed characteristic or condition may be a value or an index (e.g., DAI), for example, a flow rate, a concentration, a cell population (e.g., a change in white blood cell locations or characteristics), or any combination thereof, which in turn may be analyzed by a suitable technique. For example, a relative change exceeding a threshold may be used to determine if the modulation parameters are modified. The desired modulation may be assessed via a measured clinical outcome, such as a presence or absence of an increase in tissue structure size (e.g., colon tissue characteristics) or a change in concentration of one or more released molecules (e.g., relative to the baseline concentration before the neuromodulation). In one embodiment, a desired modulation may involve an increase in concentration above a threshold, e.g., above a about 50%, 100%, 200%, 400%, 1000% increase in concentration relative to baseline. For blocking treatments, the assessment may involve tracking a decrease in concentration of a molecule over time, e.g., at least a 10%, 20%, 30%, 50%, or 75% decrease in the molecule of interest. Further, for certain subjects, the desired blocking treatment may involve keeping a relatively steady concentration of a particular molecule in the context of other clinical events that may tend to increase the concentration of the molecule. That is, desired blocking may block a potential increase. The increase or decrease or other induced and measurable effect may be measured within a certain time window from the start of a treatment, e.g., within about 5 minutes, within about 30 minutes. In certain embodiments, if the neuromodulation is determined to be desired, the change in the neuromodulation is an instruction to stop applying energy pulses. In another embodiment, one or more parameters of the neuromodulation are changed if the neuromodulation is not desired. For example, the change in modulation parameters may be an increase in pulse repetition frequency, such as a stepwise increase in frequency of 10-100 Hz and assessment of the desired characteristic until a desired neuromodulation is achieved. In another implementation, a pulse width may be changed. In other embodiments, two or more of the parameters may be changed together, in parallel or in series. If the neuromodulation is not desired after multiple parameter changes, the focus (i.e., the site) of energy application may be changed.

In one example, the present techniques may be used to treat a subject with improved IBD-like symptomology to improve stool consistency, gross bleeding/diarrhea and colon tissue integrity. In IBD, various etiological factors disturb the delicate homeostasis of immune cells in the intestines, e.g., T1, T2, T17, Treg, which can generate a cascade of inflammatory cytokines via activated macrophages and dendritic cells in a self-sustaining cycle. Some notable candidates include tumor necrosis factor-alpha (TNF-α), interferon-gamma (IFN-γ), interleukin-(IL-)17, IL-22, IL-1, IL-6, IL-8, IL-12 and IL-18. These inflammatory cytokines can incite benign local inflammatory responses, but uncontrolled overproduction can provoke tissue injury, diffocus ultrasounde coagulation, death and/or hypotension. With this in mind, mitigating dysregulated cytokine levels in intestinal inflammation and tissue injury may be accomplished via the cholinergic anti-inflammatory pathway (CAP). Targeting the celiac plexus facilitated selectively differentiation between the splenic ('systemic') versus enteric ('local') cholinergic anti-inflammatory pathway and activation of the enteric CAP at different locations within the mesentery comprising the superior mesenteric ganglion, celiac ganglion, inferior mesenteric ganglion, dorsal root ganglion, or myenteric plexus. In certain embodiments, the disclosed techniques permit activation of the enteric CAP without activation of the splenic CAP or with relatively lower activation of the splenic CAP. The present techniques provide advantages over electrical vagus neurostimulation devices that have been shown to require the spleen/splenic ganglion as a pathway for enteric neuron activation. The present techniques precisely modulate the enteric pathway rather than the splenic pathway. In certain embodiments, the activation may be systemic/splenic, local/enteric, or mixed/combined stimulation. Selection of CAP stimulation sites targeting specific peripheral ganglia versus direct activation of the myenteric plexus, and selecting particular ultrasound stimulus parameters including power, duration, and dose timing of the stimulus can be further delineated for IBD therapeutic optimization.

The present techniques demonstrated reduction in IBD symptoms in given mild (5%) and more severe (7%) DSS while focused ultrasound is applied once or twice daily, respectively. Targeting the celiac plexus resulted in focused ultrasound efficacy for IBD symptomology. The celiac plexus is a group of nerves responsible for sending messages from the pancreases, liver, kidney, gall bladder, spleen, and bowels. There are four major ganglions associated with the celiac plexus and the examples disclosed targeted the upper section of the celiac plexus compromising the celiac ganglions, and the superior mesenteric ganglion. The superior mesenteric ganglion is responsible for innervating the intestines, which makes it an ideal target for focused ultrasound to treat IBD. Both the left and right celiac ganglia also play a role bowel innervation, but these ganglia are also associated with liver activity. In the rat, the superior mesenteric ganglion was measured to be approximately 3 mm from the celiac ganglions. Given that the transducer is ~20 mm in diameter with a focal point of 1 mm, accurate placement of the transducer on this plexus was a factor in success. Off-target focused ultrasound may explain why some animals exhibited much better stool consistency, bloody stool and colon length with focused ultrasound than others. Along similar considerations, animal breathing under isoflurane anesthesia can cause chest movement and alteration in the focal point of the transducer with subsequent mis-targeting of the celiac plexus. In addition, this may also explain the weight loss observed with focused ultrasound since neuromodulation in specific abdominal locations may result in the direct activation of incretin pathways within the gastrointestinal system. Accordingly, accounting for breath-induced movement may improve targeting. Further, such variability may point to advantages in using relatively smaller transducers with more targeted (focused) and less diffuse effects.

Technical effects of the disclosed embodiments include techniques for non-invasive focused ultrasound on the celiac plexus to reduce effects of IBD, such as bloody stools, to improve stool consistency and to protect tissue length and integrity. The present techniques may be used to treat patients who are nonresponsive to pharmaceutical interventions or to augment pharmaceutical or surgical interventions.

This written description uses examples, including the best mode, and also to enable any person skilled in the art to practice the disclosed embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
   an ultrasound probe configured to apply focused ultrasound energy to a region of interest comprising at least a portion of a celiac plexus in a subject to neuromodulate a peripheral ganglion of the celiac plexus of the subject; and
   a controller configured to:
   acquire image data of the subject from the ultrasound probe operating in an imaging mode;
   identify anatomical landmarks in the image data, wherein the anatomical landmarks comprise a junction of at least one of a hepatic artery and splenic artery with an abdominal aorta;
   automatically select the region of interest based on the anatomical landmarks adjacent to the peripheral ganglion of the celiac plexus identified in the image data;
   control the ultrasound probe to apply the focused ultrasound energy to the region of interest as part of a treatment protocol to treat inflammatory bowel disease in the subject, wherein applying the focused ultrasound energy to the region of interest causes a change in concentration of one or more molecules of interest in the subject relative to a baseline concentration, wherein the one or more molecules of interest comprises one or more of interleukin (IL)-1, tumor necrosis factor (TNF-a), or interferon-gamma (IFN-y); and
   detect the change in concentration.

2. The system of claim 1, wherein the ultrasound probe comprises a therapy transducer configured to apply the focused ultrasound energy and an imaging probe configured to acquire the image data.

3. The system of claim 1, wherein the region of interest comprises at least a portion of a peripheral ganglion of the celiac plexus.

4. The system of claim 1, wherein the treatment protocol comprises applying the ultrasound energy to the region of interest at least daily over a plurality of days.

5. The system of claim 1, wherein the controller is configured to:
   cause a display of the image data;
   receive a user input indicative of the region of interest in the displayed image data; and
   select the region of interest based on the user input.

6. The system of claim 1, wherein the one or more molecules of interest further comprises perinuclear anti-neutrophil antibody, anti-*Saccharomyces Cerevisiae* antibody, calprotectin, C-reactive protein, or anti-flagellin antibody.

7. The system of claim 1, wherein applying the focused ultrasound energy to the region of interest causes enteric cholinergic anti-inflammatory pathway (CAP) stimulation.

8. The system of claim 7, wherein applying the focused ultrasound energy to the region of interest does not cause splenic CAP stimulation or causes relatively less splenic CAP stimulation relative to enteric CAP stimulation.

9. The system of claim 1, comprising assessing a response to the focused ultrasound energy over a period of time; and changing a treatment protocol to change a dose frequency based on the assessing.

10. The system of claim 1, wherein applying the focused ultrasound energy to the region of interest results in an improvement of a DAI score of the subject relative to a baseline DAI score, wherein the baseline DAI score is determined prior to the applying.

11. A method, comprising:
    acquiring image data of a subject from an ultrasound probe operating in an imaging mode, wherein the subject is diagnosed with inflammatory bowel disease;
    identifying anatomical landmarks in the image data, wherein the anatomical landmarks comprise a junction of at least one of a hepatic artery and splenic artery with an abdominal aorta;
    automatically selecting a region of interest comprising at least a portion of a celiac plexus based on the anatomical landmarks adjacent to a peripheral ganglion of the celiac plexus identified in the image data; and
    controlling the ultrasound probe to apply focused ultrasound energy to the region of interest as part of a treatment protocol to treat the inflammatory bowel disease, wherein the region of interest comprises at least a portion of the peripheral ganglion of the celiac plexus, wherein applying the focused ultrasound energy to the region of interest causes a change in concentration of one or more molecules of interest in the subject relative to a baseline concentration, wherein the one or more molecules of interest comprises one or more of interleukin (IL)-1, tumor necrosis factor (TNF-a), or interferon-gamma (IFN-y); and
detecting the change in concentration.

12. The method of claim 11, wherein the one or more molecules of interest further comprises one or more of IL-12 or IL-10.

13. The method of claim 11, wherein the subject has a diagnosis of Crohn's disease.

14. The method of claim 11, wherein the subject has a diagnosis of ulcerative colitis.

15. The method of claim 11, wherein applying the focused ultrasound energy to the region of interest results in an improvement of a disease activity index (DAI) score of the subject relative to a baseline DAI score, wherein the baseline DAI score is determined prior to the applying.

16. The method of claim 11, wherein applying the focused ultrasound energy to the region of interest results in a reduction in a stool blood level relative to a baseline stool blood level determined prior to the applying.

* * * * *